(12) United States Patent
Kashanin et al.

(10) Patent No.: US 11,839,876 B2
(45) Date of Patent: Dec. 12, 2023

(54) APPARATUS FOR MICROFLUIDIC FLOW CYTOMETRY ANALYSIS OF A PARTICULATE CONTAINING FLUID

(71) Applicant: Cellix Limited, Dublin (IE)

(72) Inventors: Dmitry Kashanin, Dublin (IE); Igor Shvets, Dublin (IE); Francesco Dicorato, Dublin (IE)

(73) Assignee: Cellix Limited, Dublin (IE)

( * ) Notice: Subject to any disclaimer, the term of this patent is extended or adjusted under 35 U.S.C. 154(b) by 1264 days.

(21) Appl. No.: 16/303,929

(22) PCT Filed: May 24, 2017

(86) PCT No.: PCT/EP2017/062574
§ 371 (c)(1),
(2) Date: Nov. 21, 2018

(87) PCT Pub. No.: WO2017/202932
PCT Pub. Date: Nov. 30, 2017

(65) Prior Publication Data
US 2020/0316603 A1     Oct. 8, 2020

(30) Foreign Application Priority Data

May 24, 2016    (EP) .................................... 16171121

(51) Int. Cl.
    *B01L 3/00*         (2006.01)
    *G01N 15/14*      (2006.01)

(52) U.S. Cl.
    CPC ... *B01L 3/502776* (2013.01); *B01L 3/502761* (2013.01); *G01N 15/1404* (2013.01);
(Continued)

(58) Field of Classification Search
CPC ......... B01L 3/502776; B01L 3/502761; B01L 2200/0636; G01N 15/1404; G01N 2015/1413; G01N 2015/149
See application file for complete search history.

(56) References Cited

U.S. PATENT DOCUMENTS

| | | | |
|---|---|---|---|
| 2009/0066936 | A1 | 3/2009 | Huang et al. |
| 2015/0024373 | A1 | 1/2015 | Xia et al. |

FOREIGN PATENT DOCUMENTS

| | | | |
|---|---|---|---|
| EP | 2 995 961 A1 | 3/2016 | |
| GB | 2 383 127 A | 6/2003 | |

(Continued)

OTHER PUBLICATIONS

Gawad S. et al. "Micromachined Impedance Spectroscopy Flow Cytometer for Cell Analysis and Particle Sizing", Lab on a Chip: Miniaturisation for Chemistry, Physics, Biology, Materials Science and Bioengineering, Royal Society of Chemistry, GB, vol. 1, Jan. 1, 2001, pp. 76-82.

(Continued)

*Primary Examiner* — Brian J. Sines
(74) *Attorney, Agent, or Firm* — Bookoff McAndrews, PLLC

(57) ABSTRACT

An apparatus for microfluidic flow cytometry analysis of a particulate containing fluid An apparatus for microfluidic flow cytometry analysis of a particulate containing fluid comprises a hydrodynamic focussing apparatus for providing a focused stream of particulate containing fluid; and a microfluidic chip. The chip has a plurality of layers and comprises a microfluidic channel that extends through the chip substantially orthogonal to a plane of the layers of the chip, and is in fluid communication with the hydrodynamic focusing apparatus for receipt of a focused steam of particulate containing fluid. The chip also comprises a detection zone comprising at least one pair of electrodes in electrical (Continued)

communication with the microfluidic channel. At least one pair of electrodes comprise an excitation electrode coupled to an AC signal source and a detection electrode configured to detect AC impedance changes in the microfluidic channel between the electrodes resulting from particles passing between the electrodes in the microfluidic channel. Methods of sorting mammalian sperm cells according to sex is also described.

15 Claims, 13 Drawing Sheets

(52) U.S. Cl.
CPC .......... *B01L 2200/0636* (2013.01); *B01L 2200/0689* (2013.01); *B01L 2300/0627* (2013.01); *B01L 2300/0645* (2013.01); *B01L 2300/0809* (2013.01); *G01N 2015/149* (2013.01); *G01N 2015/1413* (2013.01); *G01N 2015/1415* (2013.01)

(56) References Cited

FOREIGN PATENT DOCUMENTS

| WO | WO 2006/037561 A1 | 4/2006 |
| WO | WO 2015/009284 A1 | 1/2015 |

OTHER PUBLICATIONS

International Search Report and Written Opinion in International Application No. PCT/EP2017/062574 dated Jan. 25, 2018 (16 pages).

APPARATUS FOR MICROFLUIDIC FLOW CYTOMETRY ANALYSIS OF A PARTICULATE CONTAINING FLUID

TECHNICAL FIELD

The invention relates to an apparatus for microfluidic flow analysis of a particulate containing fluid. In particular, the invention relates to an apparatus for microfluidic flow cytometry analysis of a cell containing fluid, and sorting of cells in a fluid containing different sub-populations of cells. The invention also relates to a method of analysis of a particulate containing fluid, and a method of sorting cells in a fluid containing different subpopulations of cells.

BACKGROUND TO THE INVENTION

Conventional flow cytometry makes it possible to position the cells in the center of flow channel and create uniform stream of single cells, which one-by-one pass through the focused laser beam. This is achieved by a hydrodynamic focusing setup in which the cells are injected into a capillary tube. The hydrodynamic focusing set up usually consists of two nozzles. A smaller nozzle is positioned inside the larger nozzle. Both nozzles have tapered shape. The sample fluid containing cells is injected into the smaller inner nozzle. The flow direction is towards the tapered end of the nozzle. The sheath fluid is injected into the space between the outer surface of the inner nozzle and the inner surface of the outer nozzle; the direction of flow of the sample fluid and the sheath fluid is the same. Both flows are laminar. The operation is based on injecting the sample fluid into the laminar flow of the sheath fluid. This squeezes the stream of cells in the sample fluid radially. Hydrodynamic focusing is known for decades. The phenomenon was described as early as in the year 1883 [O. Reynolds, Proc. R. Soc. London, 1883, 35 84-99] and it was originally related to the confinement of the sample flow flanked on both sides by sheath flow streams. The cross-section of the sample liquid flow in the detection channel in a flow cytometer is typically in the range of 0.003-0.03 mm$^2$.

In flow cytometry, there is also strong interest to move away from staining the cells with a fluorescent dye as it may affect the viability of the cells and also being an additional step in the process, it adds to the costs of the cell separation. There is also drive to develop smaller size, automated systems for the cell separation as they can be used at smaller facilities. Commercial cytometers for cell separation are rather large, costly and require constant operator supervision to successfully sort cells.

Cells can also be detected without a fluorescence dye using non-optical impedance based method of electrical volume analysis as described in [3 and 4]. This method is called impedance cytometry. Hydrodynamic focusing is also essential for the impedance cytometry. Indeed, for cell identification it is necessary to arrange the cells in such a flow that they pass in front of the detection system one by one. This "one cell-by-one cell" principle is fundamental for the successful cell identification: one needs to avoid the situation of multiple cells passing through the detection system at once as it could prevent the identification. Making the channel so small that cell align there one by one due to the tight cross-section of the channel, is not practical: such a small channel that is comparable in cross-section with a single cell, is prone to blockage and it would also require a significant pressure difference as the friction of the laminar flow against the walls increases with decreasing channel cross-section. Therefore, it is common to use hydrodynamic focusing.

Microfluidic hydrodynamic focusing is based on injection of the sample fluid into the laminar flow of sheath fluid in the microfluidic chip. The two flows then merge into to a single channel, usually of a reduced cross-section. This reduces the cross-sections of both, the sheath fluid part of the flow and also the sample liquid flow, and thus achieves the desired reduction in the cross-section of the sample fluid flow. To control the cross-section of the sample fluid, one could change the flow rates of the sample fluid and sheath fluid. For example, the flow rate of the sheath fluid could be increased to reduce the cross-section of the sample fluid. Such a small cross-section of the sample fluid flanked by the flow of the sheath fluid passes through a channel of a rather large cross-section, i.e. multiple of the cell size, that does not block. One could say that microfluidic focusing replaces the hard walls of microfluidic channel for fluid quasi-walls and this reduces the risk of the microchannel blocking. In relation to the electrical impedance based cytometry, hydrodynamic focussing reduces the width of the conductive sample stream to the appropriate size of the cells, increasing the percentage resistance change in the conductive path when a cell passes by.

In recent years, microfluidic impedance cytometry has been further developed to count and discriminate between different kinds of cells. Multi-frequency impedance measurements can be used to determine the electrical properties of single cells in a microchip [5 and 6]. In these methods cells flow between miniature electrodes which have an AC field applied across them. As the cell passes between the electrodes, the current path is disturbed and the change in current gives a change in the impedance signal associated with a single cell. Usually, impedance measurements at the frequency of (1-5 MHz) give information on the cell membrane capacitance whilst much higher frequencies (>10 MHz) probe the internal properties of the cell. Two or more frequencies can be applied simultaneously to differentiate different types of cells. Impedance flow cytometry can readily detect a cell, but when it comes to more challenging task of separating the sub-populations of cells within the sample fluid, the performance of the impedance cytometry is much less convincing due to large spread in the data points corresponding to each cell. The theoretical rationale underpinning the measurements can be summarized as follows. The impedance response can be represented by two constituents: the real and imaginary components. These can be measured using phase-sensitive detection techniques using e.g. lock-in amplifier. These measurements represent information on the real and imaginary part of the dielectric function of the cell (particle). Such measurements of the frequency-dependent dielectric function of the cell contain valuable information specific to the cell (particle) and can be used as the basis for the discrimination between different types of cells (particles).

To reduce the CV of the impedance cytometry it is desirable to be able to direct the sample flow not just in the middle of the channel but e.g. through a point that is located closer to one of the electrodes (e.g. excitation electrode). It may also be desirable to align all the cells in the same particular way with respect to the direction of the electric field created by the electrodes. The semen cells do not have an overall spherical shape but are rather elongated in shape. The signal from the cell in electrical impedance cytometry device depends on the orientation of the elongated axis of the cell with respect to the electrodes.

In recent years there is increasing body of work on the use of hydrodynamic focusing in microfluidic chips and microchannels. For example, patent JP2003-107099 [7] discloses a "fractionation microchip having a channel for introducing a particulate-containing solution, and a sheath flow forming channel arranged on at least one lateral side of the introducing channel. The fractionation microchip further has "a particulate measuring section for measuring the particulates introduced, at least two particulate fractionating channels disposed on the downstream side of the particulate measuring section so as to perform fractional collection of the particulates, and at least two electrodes disposed in the vicinity of channel ports opening . . . so as to control the moving direction of the particulates." The particulate fractionation microchip disclosed in patent JP2003-107099 [7], is so designed that fluid laminar flows are formed by a "trifurcated channel" having a channel for introducing a particulate-containing solution and two sheath flow-forming channels. In the particulate fractionation microchip disclosed in patent JP2003-107099 [7], the trifurcated channel ensures that the particulate-containing solution is sandwiched by the flows of the sheath liquid from the left and right sides, and the particulates are made to flow through the centre of the channel in the particulate measuring section. As a result, in the case of measuring the particulates optically, for example, each of the particulates can be accurately irradiated with measuring light. Similar approach is described in [8 and 9].

The 2D hydrodynamic focusing has its intrinsic limitations. With this in mind, there is an increased effort to introduce a 3D hydrodynamic focusing on a microfluidic chip to confine the sample in both, the horizontal and vertical directions. One solution for integration of such 3D focusing with a conventional type microfluidic chip is described in [10]. The focusing is achieved by using a two-level design, the sheath fluid enters the microfluidic chip from a channel that is both, wider and taller than the sample stream.

A similar approach is described in publication "Universally applicable three-dimensional hydrodynamic microfluidic flow focussing" Chiu et al. [11]. In that publication 3D focusing refers to the confinement of sample flow to a streamline at the centre of a channel of a conventional microfluidic planar chip.

Furthermore patent US0283148 2009 Shinoda et. al. [12] describes another microchip structure. The patent teaches how to introduce the hydrodynamic focusing on a chip. This is done by inserting a microtube configured to introduce a sample liquid into a laminar flow of sheath liquid.

Once the cell population is identified, they can be separated into specific sub-populations. There are several known methods for the cell separation. For example, patent US2014/273192A1 [13] describes the method and apparatus where there is a secondary channel perpendicular to the main channel. The unsorted cells pass through the main channel and their subpopulation is identified (in this case cells are separated into subpopulations based on the content of cell DNA). Following the identification, once the cells pass in front of the secondary channel, a pressure pulse is applied delivering a pulse of force to each cell. The separation is based on the magnitude and polarity of the pressure pulse.

To summarise, shortcomings of current methods of fluorescence cytometry are the need for staining that affects the cell viability and the extra costs associated with the cell staining steps. There are ongoing efforts to address these shortcomings based on non-optical impedance cytometry.

However, the conventional Coulter-type cytometer is difficult to utilise for the separation of cells. Long distance from the aperture through which cell pass to the electrodes leads to a large variability of the cell positions as they pass the electrodes of the detection system and also variability in the cell orientations with respect to the electrodes. Detections of cells of small size may also be challenging. This stimulates development of on-chip impedance-based cytometers for the separation of cells into subpopulations. Most of these efforts described above are directed at devising the 3D hydrodynamic focusing around a conventional planar chip, i.e. the main changes are implemented to the hydrodynamic focusing part of the apparatus while the conventional planar microfluidic chip architecture is deployed.

Gawad et al [5] describes a micromachined impedance spectroscopy flow cytometer for cell analysis and particle sizing. The apparatus comprises a microfluidic chip having a planar geometry and a microfluidic channel that extends across the chip in the plane of the chip, with the result that the channel and electrodes are in the same plane and that the device is not suitable for coupling to a hydrodynamic focussing apparatus. An inability to position the cells or particles in front of the impedance detector leads to significant variation in impedance amplitudes which is observed by the authors: This is particularly illustrated by the FIG. 9 p. 80, which displays significant variation of impedance amplitudes (over 100%) for uniform population of latex beads of 5 um and 8 um respectfully. It is clear that if uniform populations produce such a variable signal than the cell populations will be distributed even more, which is also highlighted in the FIG. 11 (variation from 0.01 to 0.04 for detection of erythrocytes at 1.72 MHz).

US2005/0118705 [16] describes similar apparatus for interrogating particles using a planar MEMS chip. The device comprises a microfluidic channel that extends across the chip in a plane of the chip, and electrode pairs provided on each side of the microfluidic channel is the same plane as the channel. The device is also not suitable for coupling to a hydrodynamic focussing apparatus and therefore unable to reduce variation of impedance detection method.

EP2995961 [17] describes an analytical cartridge formed as a multilayer device and having a vessel layer and flow channel layer. It further describes a flow channel layer having electrical signal generator and electrical measurement means that measures electrical amount at predetermined position. It is further detailed by FIG. 7, where electrodes 24 a disposed either side of interconnecting channel K between channels B1 and B2 located in the layers P2 and P4 respectively. Electrical changes are then measured as cell passes the interconnecting narrowing channel K. This configuration has significant drawbacks in ability to analyse cells at high throughout rate as it has very poor spatial resolution, as electrode are not opposed to each other and separated by a significant space. Moreover in this configuration the cells also pass alongside the electrodes in channels B1 and B2, which affects the overall readout of the electrical measurement as potentially one cell can be flowing over electrode 24 in channel B1 and the other cell flowing over electrode 24 in the channel B2 at the same time. This will result in imprecise measurement of electrical properties of cells. It is also not possible to couple the device to a hydrodynamic focusing apparatus, as it has 90 degree interconnection between the channels, which will lead to defocusing of sample stream.

It is an object of the invention to overcome at least one of the above-referenced problems. In particular, it is an object of the invention to provide an apparatus for sorting cells by flow cytometry on a microfluidic chip that does not require tagging of the cells.

STATEMENTS OF INVENTION

Briefly, the Applicant has discovered that accurate sorting of cells using impedance-based flow cytometry in a microfluidic chip requires that the sample is focussed with hydrodynamic focussing prior to delivery to the microfluidic chip. However, conventional planar microfluidic chips are not suited for use with hydrodynamic focussing apparatus as it is difficult to align an outlet of a hydrodynamic focussing apparatus with a chip inlet disposed on the side of a planar chip. In addition, the planar chip architecture where a longitudinal axis of the microfluidic channel runs parallel to the plane of the layers of the chip makes it difficult to position multiple electrode pairs around a single detection plane. Furthermore, the planar microfluidic chip configuration greatly restricts the choice of possible options for the alignment of electrodes around the channel. The Applicant has overcome this problem by providing a microfluidic chip having a microfluidic channel (bore) that runs substantially orthogonal to the chip, i.e. the bore extends through the layers of the chip as opposed to across and parallel to the layers. The chip architecture facilitates coupling the hydrodynamic focussing apparatus to the microfluidic channel, and also provides greater flexibility in positioning electrode pairs within the chip by allowing electrode pairs to be disposed in different layers of the chip (detection at different points along the channel) and allowing multiple electrode pairs in a single layer by displaced radially with respect to each other (multiple detection signals at the same point along the channel).

Accordingly, in a first aspect, the invention provides an apparatus for microfluidic flow cytometry analysis of a particulate containing fluid comprising:
- a hydrodynamic focussing apparatus for providing a focussed stream of particulate containing fluid; and
- a microfluidic chip having a substantially orthogonal microfluidic channel in fluid communication with the hydrodynamic focussing apparatus for receipt of a focussed steam of particulate containing fluid and a detection zone comprising at least one pair of electrodes in electrical communication with the microfluidic channel,
- wherein the at least one pair of electrodes comprise an excitation electrode and a detection electrode configured to detect AC impedance changes in the microfluidic channel between the electrodes resulting from particles passing between the electrodes in the microfluidic channel.

In another aspect, the invention provides a microfluidic chip for microfluidic flow analysis of a particulate containing fluid, the microfluidic chip comprising:
- a plurality of layers;
- a microfluidic channel that is substantially orthogonal to a plane of the layers of the chip and is configured for fluidic engagement with a hydrodynamic focussing apparatus for receipt of a focussed stream of particulate containing fluid; and
- a detection zone comprising at least one pair of electrodes in electrical communication with the microfluidic channel,
- wherein the at least one pair of electrodes comprise an excitation electrode coupled to an AC signal source and a detection electrode configured to detect AC impedance changes in the microfluidic channel between the electrodes resulting from particles passing between the electrodes in the microfluidic channel.

In one embodiment, the focussed stream of particulate fluid comprises a core stream of particulate containing fluid having laminar flow and an annular sheath of positioning fluid having laminar flow. In one embodiment, the streams have a Reynold Number of 1-1000. In one embodiment, the streams have a Reynold Number of 10-500. In one embodiment, the streams have a Reynold Number of 50-200. Methods of measuring the Reynolds number for a stream of fluid are described in [14].

In one embodiment, the particulates are cells. Other types of particulates that can be analysed using the apparatus, chip and methods of the invention include fragments of cells like endosomes or exosomes, polymer or metal microbeads or combination of both, particles of organic or inorganic material of a micrometer range, droplets of water-based solutions in oil or any other immiscible fluids containing several fluid phases. In one embodiment, the apparatus or chip is for sorting cells according to phenotypic differences. In one embodiment, the phenotypic difference is selected from: cell type; cell sex; disease status; and cell health. In one embodiment, the apparatus, chip and methods of the invention relate to sorting of different populations of cells (for example, sorting epithelial cells from bone marrow cells). In one embodiment, the apparatus, chip and methods of the invention relate to sorting of different sub-populations of cells (for example, sorting different sub-populations of leukocyte cells). In one embodiment, the apparatus, chip and methods of the invention relate to sorting of sperm cells according to sex (for example, sorting bovine sperm cells into X and Y populations of sperm cells). In one embodiment, the apparatus, chip and methods of the invention relate to sorting of a population of cells into living cells and dead cells. In one embodiment, the apparatus, chip and methods of the invention relate to sorting of a cell population into cancerous cells and non-cancerous cells. In one embodiment, the apparatus, chip and methods of the invention relate to sorting of a population of cells into healthy cells and unhealthy cells. In one embodiment, the apparatus, chip and methods of the invention relate to sorting of a population of cells according to their age (young cells vs. mature ones).

In one embodiment, the hydrodynamic focussing apparatus is configured to provide a focussed stream of cell (or particulate) containing fluid to the microfluidic channel in which the cells (or particulates) pass the at least one electrode pair in single file. In one embodiment, the hydrodynamic focussing apparatus is configured to provide a focussed stream of cell containing fluid to the microfluidic channel in which the cells are aligned in the same direction. In one embodiment, the apparatus is configured such that non-uniformly shaped cells are aligned along a plane of detection (i.e. elongated cells such as sperm cells are aligned in a plane between the electrodes).

In one embodiment, the hydrodynamic focussing apparatus is configured to provide a focussed stream of cell containing fluid to the microfluidic channel in which the cells (or particulates) are focussed at a well-defined focal point (position) within the cross-section of the channel that is selected appropriately with respect to the electrodes of the impedance detection system to maximize the signal from the cells and the contrast between the cells (or particulates). In one embodiment, the focal point is disposed closer to one electrode than the other. In one embodiment, the focal point is disposed closer to the excitation electrode than the detection electrode.

In one embodiment, the hydrodynamic focussing apparatus is configured to provide anisotropic alignment of the particulates in the particulate containing stream so that the particulates are preferentially aligned with respect to the electrodes such that the difference in impedance responses of different particles is amplified.

In one embodiment, the detection zone comprises a plurality of pairs of electrodes, for example 2, 4, 6, 8, 10, 12, 14, 16 or 18 electrodes.

In one embodiment, the detection zone comprises a plurality of electrode pairs in the same detection plane. This is illustrated in FIG. 7 below, where the pairs of electrodes are arranged radially about the microfluidic channel in a single plane.

In one embodiment, the detection zone comprises a plurality of electrodes pairs in different detection planes. This is illustrated in FIG. 9 below, where the pairs of electrodes are arranged radially along the microfluidic channel and positioned in planes axially displaced with respect to each other.

In one embodiment, the electrode pair comprises an excitation electrode disposed in one plane and a detection electrode disposed in a second plane.

In one embodiment, the microfluidic chip comprises two or more layers, wherein the microfluidic channel is substantially orthogonal to the layers (i.e. it extends through the two or more layers). In one embodiment, the detection zone spans more than one layer. In one embodiment, the detection zone spans 2, 3, 4, 5 or 6 layers. In one embodiment, at least two of the layers comprise an electrode pair. In one embodiment, an excitation electrode of an electrode pair is disposed in one layer and a detection electrode of the same electrode pair is disposed in a second layer.

In one embodiment, the apparatus or chip comprises an electrical supply module. In one embodiment, the electrical supply module is configured to energise the excitation electrode of the at least one pair of electrodes with AC voltage in the frequency range of 100 KHz to 200 MHz.

In one embodiment, the apparatus or chip is configured such that the AC impedance change detected by the at least one pair of electrodes comprises amplitude and phase characteristics of the AC voltage induced at the detection electrode.

In one embodiment, the microfluidic chip includes a separation zone comprising a force generator configured to exert a force on the particulate containing fluid to displace an individual particulate in the stream in response to AC impedance changes corresponding to the individual particulate detected by the electrodes. In one embodiment, the microfluidic channel branches into two or more channels in the separation zone, and in which the force generator is disposed to displace one or more particulates into one or more of the channels.

In one embodiment, the microfluidic channel has a non-circular cross-section. In one embodiment, the cross-section is polygonal. In one embodiment, the cross-section is square. In one embodiment, the cross-section is rectangular.

In one embodiment, the hydrodynamic focussing device is configured to provide a focussed stream of particulate containing fluid in which one or both of the core stream and positioning stream has an elongated cross section. Examples are illustrated in FIGS. 10-13.

In one embodiment, the elongated stream is elongated in the plane of the at least one pair of electrodes. An example is illustrated in FIG. 12.

In one embodiment, the elongated stream is elongated in a plane perpendicular to a plane of the at least one pair of electrodes. An example is illustrated in FIGS. 10-13.

In one embodiment, the hydrodynamic focussing device is configured to provide a focussed stream of particulate containing fluid in which a longitudinal axis of the particulate (core) stream is offset with respect to a longitudinal axis of the positioning stream. Examples are illustrated in FIGS. 12 and 13.

In one embodiment, the hydrodynamic focussing device is configured to provide a focussed stream of particulate containing fluid in which the longitudinal axis of the particulate (core) stream is offset towards the excitation electrode. In one embodiment, the hydrodynamic focussing device is configured to provide a focussed stream of particulate containing fluid in which the longitudinal axis of the particulate (core) stream is offset towards the detection electrode.

In one embodiment, the cross-sectional area of the microfluidic channel in the detection zone is in the range of 0.0001-0.09 mm$^2$. In one embodiment, the microfluidic channel has a cross-sectional area of 0.01-0.09 mm$^2$. In one embodiment, the microfluidic channel has a cross-sectional area of 0.0025-0.01 mm$^2$. In one embodiment, the microfluidic channel has a cross-sectional area of 0.0001-0.0025 mm$^2$. In one embodiment, the cross-section of the microfluidic channel varies along the length of the channel.

In one embodiment, the apparatus or chip is configured to provide a flow rate of the core stream of particulate fluid of 0.1-100 μL per minute.

In one embodiment, the apparatus or chip is configured to provide a flow rate of the positioning stream of fluid of 1-1000 μL per minute.

In one embodiment, the detection zone of the apparatus or chip contains at least two optical waveguides, at least one of these is coupled to a light source and the other one is coupled to an optical detector to detect optical signal resulting from the particulates and such optical signal is measured in conjunction with the electrical signal detected at the detection electrode to improve the CV of the data points from a population of particulates.

In one embodiment, the apparatus or chip is configured such that the AC signal is composed of at least two different frequencies and is applied to the excitation electrodes, and the detection electrodes detect impedance change caused by single passing particulates at these very same frequencies and a particulate is attributed to A or B sub-population on the basis of amplitude and phase signals detected at the detection electrodes at each of these frequencies.

In one embodiment, the particulates are cells having different phenotypes and in which the apparatus is configured to sort the cells according to phenotype.

In one embodiment, the particulates are cells of at least two different cell types.

In one embodiment, the particulates are cells of the same type having at least two different phenotypes.

In one embodiment, the electrodes have a thickness of 5-300 μm.

In one embodiment, the detection zone is disposed 100 to 2000 μm from a tip of the hydrodynamic focussing device. This is referred to below as a "spacer zone".

In one embodiment, the microfluidic chip and hydrodynamic focussing apparatus are modified to allow nested engagement and alignment there between. Alignment means that when engaged the nozzle engages with an inlet of the microfluidic channel. In one embodiment, the microfluidic chip and hydrodynamic focussing apparatus have shoulder sections configured to engage in a nested manner for alignment of the chip and hydrodynamic focussing apparatus. In one embodiment, the layers of the chip are modified to allow nested engagement there between and, in one embodiment, comprise shoulder sections configured to engage in a nested manner for alignment of the different layers of the chip.

In one embodiment, the microfluidic channel is straight. In one embodiment, the microfluidic channel in the detection zone is straight. In one embodiment, the cross-section of the microfluidic channel in the detection zone is uniform.

It will be appreciated that a longitudinal axis of the bore in the hydrodynamic focussing device is co-axial with the microfluidic channel in the microfluidic chip and the channel and bore and coupled together to form one continuous hermetically sealed channel.

The invention also provides a method for analysis of a particulate containing fluid comprising the steps of
focussing a stream of the particulate containing fluid using a hydrodynamic focussing device to provide a focussed stream comprising a core particulate containing stream and a positioning stream of fluid forming a sheath around the core stream;
passing the focussed stream along a microfluidic channel in a layered microfluidic chip in which the microfluidic channel is substantially orthogonal to the layers of the chip, and in which the microfluidic channel comprises a detection zone comprising at least one pair of electrodes configured to detect AC impedance changes in the focussed stream corresponding to particulates passing the electrodes.

The invention also provides a method for sorting cells (for example sperm cells, for example sorting sperm cells according to sex) using microfluidic cell cytometry comprising the steps of focussing a stream of the cell containing fluid using a hydrodynamic focussing device to provide a focussed stream comprising a core cell containing stream and a positioning stream of fluid forming a sheath around the core stream;
passing the focussed stream along a microfluidic channel in a layered microfluidic chip in which the microfluidic channel is substantially orthogonal to the layers of the chip, and in which the microfluidic channel comprises a detection zone comprising at least one pair of electrodes configured to detect AC impedance changes in the focussed stream corresponding to single cells passing the electrodes, and a separation zone comprising a force generator configured to displace single cells perpendicular to the direction of flow of the focussed stream in response to the AC impedance changes detected by the at least one pair of electrodes.

The invention also provides a method for sorting sperm cells according to sex using microfluidic cell cytometry comprising the steps of:
focussing a stream of the sperm cell containing fluid using a hydrodynamic focussing device to provide a focussed stream comprising a core sperm cell containing stream and a positioning stream of fluid forming a sheath around the core stream;
passing the focussed stream along a substantially orthogonal microfluidic channel in a microfluidic chip, in which the microfluidic channel comprises a detection zone comprising at least one pair of electrodes configured to detect AC impedance changes in the focussed stream corresponding to single sperm cells passing the electrodes, and a separation zone comprising a force generator configured to displace single sperm cells perpendicular to the direction of flow of the focussed stream in response to the AC impedance changes detected by the at least one pair of electrodes;
detecting the sex of single passing sperm cells in the detection zone by correlating detected AC impedance changes corresponding to the single passing sperm cells with sex; and displacing single sperm cells according to sex in the separation zone.

In one embodiment, the microfluidic chip comprises at least two pairs of electrodes, and wherein an AC signal composed of at least two different frequencies is applied to the excitation electrodes, and wherein the detection electrodes detect impedance change caused by single passing particulates at these very same frequencies and a particulate is attributed to a sub-population of particulates on the basis of amplitude and phase signals detected at the detection electrodes at each of these frequencies.

In one embodiment, the at least two pairs of electrodes are disposed on the same detection plane.

In one embodiment, the at least two pairs of electrodes are disposed on different detection planes.

In one embodiment, at least one of the excitation electrodes are disposed on a first detection plane and at least one of the detection electrodes are disposed on a different detection plane.

A method according to the invention that employs an apparatus or chip according to the invention.

In one embodiment, the apparatus and chip is configured for use with larger particulates such as fish eggs and plant and vegetable seeds having an average diameter in the mm range. In this case, the chip forming part of the apparatus and methods of the invention is a non-microfluidic chip, suitable for conveying the larger particulates. Thus, the invention also relates to the apparatus, chip and methods of the invention in which the chip is a non-microfluidic chip. Thus, the methods of the invention also relate to analysis of a population of larger particulates to separate the population into distinct sub-populations using an apparatus and chip of the invention and based on electrical impedance-based flow cytometry. For example, fish eggs or seeds may be separated into viable and non-viable sub-populations.

Thus, the invention also relates to an apparatus for flow cytometry analysis of a larger particulate containing fluid comprising:
optionally, a hydrodynamic focussing apparatus for providing a focussed stream of larger particulate containing fluid; and
a non-microfluidic chip having a substantially orthogonal fluidic channel in fluid communication with the hydrodynamic focussing apparatus for receipt of a focussed steam of larger particulate containing fluid and a detection zone comprising at least one pair of electrodes in electrical communication with the channel,
wherein the at least one pair of electrodes comprise an excitation electrode and a detection electrode configured to detect AC impedance changes in the channel between the electrodes resulting from particles passing between the electrodes in the channel.

In another aspect, the invention provides a non-microfluidic chip for flow analysis of a larger particulate containing fluid, the non-microfluidic chip comprising:
a plurality of layers;
a fluidic channel that is substantially orthogonal to a plane of the layers of the chip and is optionally configured for fluidic engagement with a hydrodynamic focussing apparatus for receipt of a focussed stream of larger particulate containing fluid; and
a detection zone comprising at least one pair of electrodes in electrical communication with the channel, wherein the at least one pair of electrodes comprise an excitation electrode coupled to an AC signal source and a detection electrode configured to detect AC impedance changes in the channel between the electrodes resulting from larger particles passing between the electrodes in the channel.

Other aspects and preferred embodiments of the invention are defined and described in the other claims set out below.

BRIEF DESCRIPTION OF DRAWINGS

FIG. 5a 3D view of section 11 of the microfluidic chip containing the 3D focusing nozzle FIG. 5b 3D view of the section 12 of the microfluidic chip containing the electrodes FIG. 5c 3D view of the section 13 of the microfluidic chip.

DESCRIPTION OF THE PREFERRED EMBODIMENTS

Figure 1A:
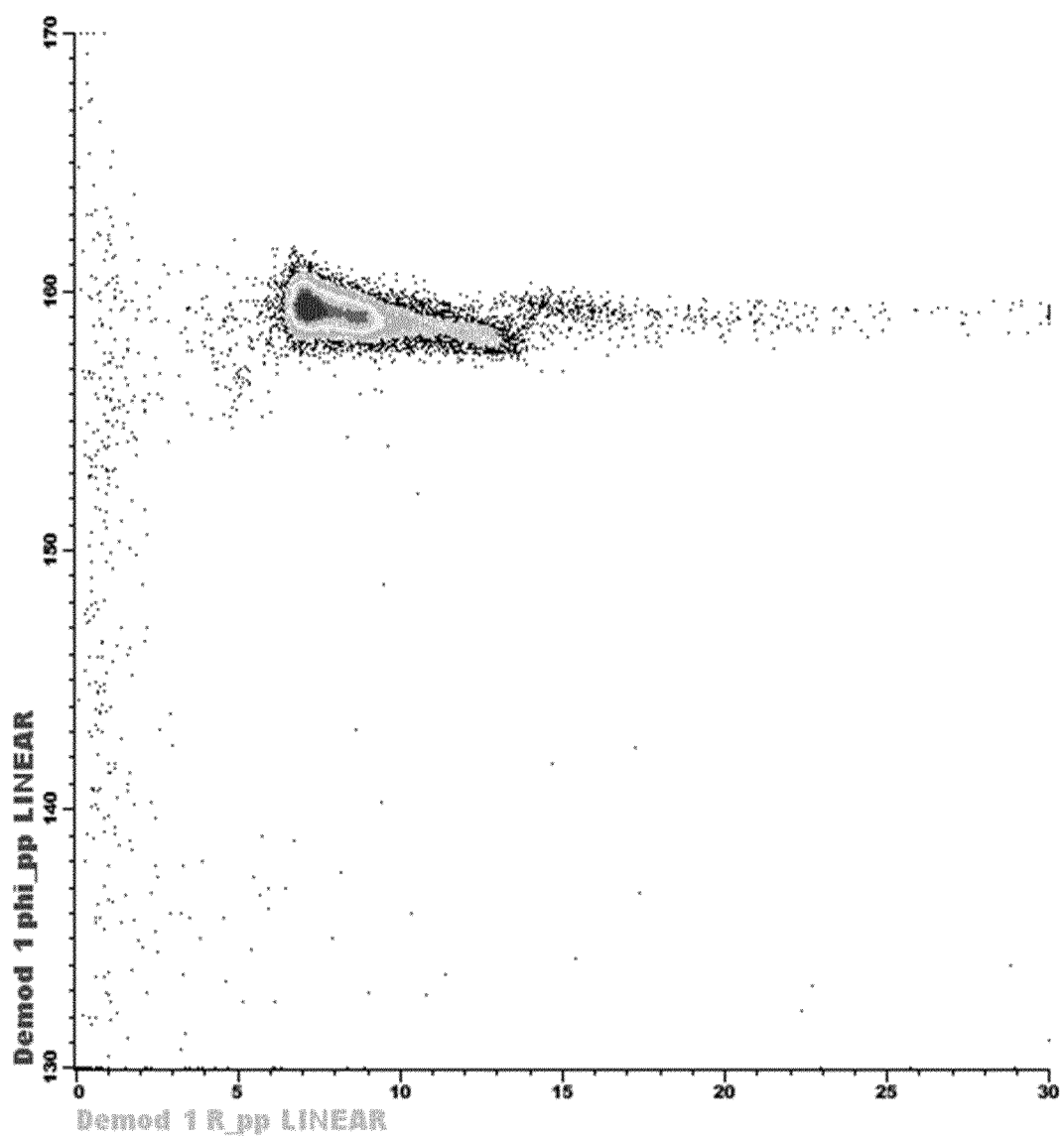
FIG. 1a. Scatter plot of data points resulting from measurements of a population of cells consisting of two sub-populations where such cells travel in a poorly focused flow though the detection zone. The separation of the cells into two sub-populations is not possible in this case.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

In the context of this specification, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

"Particulate" as applied to a particulate containing fluid means a solid body in the fluid. Examples include cells, bacteria, fungi, exosomes, endosomes and various large fragments of cells; polymer microbeads, metallic microbeads, micrometer size particles of various organic and inorganic materials. In one embodiment, the cells are sperm cells, typically human sperm cells. Likewise, "particulate containing fluid" means a fluid containing particulates. Examples include cell containing fluids, such as sperm containing fluid. "Larger particulates" means particulates having an average dimension of at least 1 mm, 2 mm, 3 mm, 4 mm or 5 mm. Examples of larger particulates include fish eggs (i.e. salmon or trout eggs) and plant seeds.

"Analysis" means determining a qualitative or quantitative characteristic of the particulates in the fluid, for example determining whether the particulates are a homogenous population or a heterogeneous population, determining the amount or concentration of particulates, or differentiating or sorting the particulates based on differences. Thus, the term broadly covers analysis of the particulates (i.e. cells) qualitatively or quantitatively, or differentiation or sorting of the particulates based on detected impedance response differences.

"Cells" means any type of cell, including mammalian cells such as sperm, white blood cells, red blood cells, bone marrow cells, immune system cells, epithelial cells, nerve cells, pulmonary cells, vascular cells, hepatic cells, kidney cells, skin cells, stem cells, or bacterial and fungal cells and hybridomas. Generally, the particulate containing fluid contains at least two different types of particulates, for example different cell types, sperm of different sex, sub-populations of the same cell types, the same cell type having different phenotypes, dead and living cells, diseased and non-diseased cells. The apparatus and methods of the invention may be employed to analyse and/or differentiate and/or separate these different types or phenotype of particulates/cells.

"Different phenotypes" as applied to cells means different populations of cells (i.e. hepatic cells and vascular cells), different sub-populations of the same cell type (i.e. different types of cartilage cells), different phenotypes of the same cell type (i.e. cell expressing different markers, diseased and healthy cells, transgenic and wild-type cells, stem cells at different stages of differentiation).

"X and Y population" as applied to sperm cells means male sperm and female sperm cells.

"Focussed stream of particulate containing fluid" means a fluid containing particulates in the form of a core stream containing the particulates and a positioning stream that at least partially, and ideally fully, embraces the core stream. In one embodiment the particulates in the core stream are focussed into a single file arrangement. In one embodiment, the cells in the core stream are aligned in the same direction.

"Microfluidic chip" means a chip having at least one microfluidic channel having a cross-sectional area of less than 1 mm$^2$ and a length of at least 1 mm. In one embodiment, the microfluidic chip has at least one microfluidic channel having a cross-sectional area of less than 0.25 mm$^2$. In one embodiment, the microfluidic chip has at least one microfluidic channel having a cross-sectional area of less than 0.01 mm$^2$. In one embodiment, the microfluidic chip has at least one microfluidic channel having a cross-sectional area of less than 0.0025 mm$^2$. In one embodiment, the microfluidic chip has a plurality of microfluidic channels, for example at least 2, 3, 4, 5, 6, 7, 8, 9 or 10 microfluidic channels. In one embodiment, the microfluidic chip has at least one microfluidic channel having a length of at least 1.500 mm. In one embodiment, the microfluidic chip has at least one microfluidic channel has a length of at least 2 mm. In one embodiment, the microfluidic chip has a length of at least 3 mm. In one embodiment, the microfluidic chip comprises a plurality of layers, for example at least 2, 3, 4, 5, 6, 7, 8, 9 or 10 layers. In one embodiment, the chip is planar.

The term "non-microfluidic chip" means a chip that is larger than a microfluidic chip and comprises a fluidic channel suitable for analysis of larger particulates such as fish eggs and plant seeds. The non-microfluidic chip typically has at least one fluidic channel having a cross-sectional area of greater than 1, 5, 10, 15 or 20 cm$^2$ and typically a length of at least 1, 5, 10, 15 or 20 cm.

"Layered chip" means a chip, typically a microfluidic chip, comprising a plurality of layers. In one embodiment, the chip is a planar chip, and the plane of the layers is the same as the plane of the chip.

"Substantially orthogonal" as applied to the microfluidic or fluidic channel means that the (micro)fluidic channel runs through the chip as opposed to parallel to the layers of the chip. The channel may be perpendicular to the layers of the chip, or run through the layers of the chip at an angle, for example at an angle of 60° or 70° to a longitudinal axis of the layers of the chip. Methods for forming substantially orthogonal microfluidic channels in a microfluidic chip are described below and include photolithography with the use of SU-8 photopolymer, where layers of the chip individually produced, electrodes subsequently sputtered through the photolithographic mask and the layers are bonded together using thermal bonding, ultrasonic bonding, adhesive or other bonding methods. In one embodiment, the (micro)fluidic channel is substantially orthogonal to a plane of the chip. In one embodiment, the (micro)fluidic channel has a uniform cross section. In one embodiment, the (micro)fluidic channel is straight.

"AC impedance changes" should be understood to mean changes in impedance detected at the detection electrode. The changes may include changes in amplitude, phase, or amplitude and phase of the signal.

"In electrical communication with the microfluidic channel" as applied to the electrodes means that electrodes are in direct electric contact with the fluid.

Figure 7:
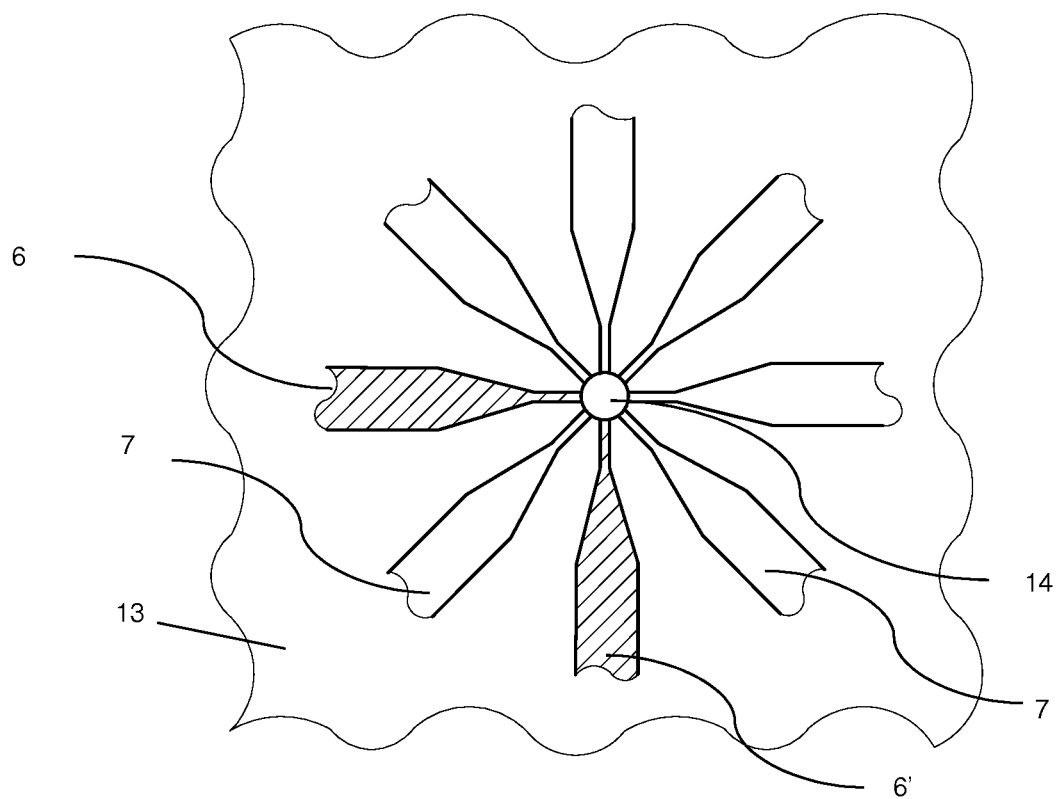
FIG. 7 Cross section of the detection zone in an embodiment having eight electrodes: two of these are excitation electrodes and six are detection electrodes.

"Detection plane" means a cross-section of the microfluidic channel (or fluidic channel) at which an electrode pair is located. The apparatus of the invention allows for a plurality of electrode pairs to be disposed at the same detection plane (as shown in FIG. 7), where the electrode pairs are spaced apart radially around the channel in the same plane. It also allows for a plurality of electrode pairs to be provided at different detection planes (see for example FIG. 8), where the electrode pairs are spaced apart axially along the channel.

"Separation zone" is a part of the microfluidic or fluidic chip, distal of the detection zone, where particulates in the fluid can be separated based on the AC impedance changes in the channel caused by the particulates in the detection zone. The separation zone generally include a force generator operably connected to the electrode pair and configured to exert a force on the particulates in response to signals from the detection zone, to separate the one or more particulates from the stream of fluid. Examples of suitable force generators for use in cell sorting apparatus are well known in the art and described for example in [15]. In one embodiment, the apparatus will typically include a processor operably connected to the at least one electrode pair and the force generator and configured to actuate the force generator in response to a signal received from the electrode pair. The actuating signal may be pre-programmed into the processor, and may vary from cell type to cell type.

"Anisotropic alignment" as applied to a focused stream of cells means that all (or substantially all) of the cells are directionally aligned to favor increased AC impedance change in the detection zone. This is particularly important for non-uniform cells, such as sperm cells, which is preferable to have the cells anisotropically aligned in the detection zone. Methods for providing anisotropic alignment of cells are described below.

This invention relates to the field of identification, differentiation and sorting of cells. In particular, the invention deals with a novel method of cell differentiation and identification that does not require a fluorescence labelling of cells, in contrast to conventionally used methods where such labelling is common. The apparatus and methods use impedance spectroscopy in a microfluidic channel in combination with hydrodynamic focusing. One aspect of the invention is the configuration of the microfluidic chip that allows for precise positioning and alignment of the cells with respect to the detection and excitation electrodes thus enabling accurate identification of different cell types. The purpose of conventional hydrodynamic focusing in a cell cytometer is organizing the cells into a train so that cells pass through the detection area in a one-by-one fashion and their identification is done following "one cell at a time" protocol. The hydrodynamic focusing is normally used in large scale cytometers that do not utilise microfluidic chip technology. Transferring these processes to microfluidic chip format is still a technical challenge. The conventional microfluidic chips can also be integrated with hydrodynamic focusing. We demonstrate the shortcomings of the available methods of hydrodynamic focusing for the purpose of identification and sorting of sperm cells in microfluidic chips using impedance detection, and describe the chip and configuration of the electrodes that can be integrated with a hydrodynamic focusing apparatus and is free from these shortcomings. In a preferred embodiment, the invention allows achieving three benefits enabling accurate identification of the cells using the impedance detection. Firstly, the train of cells is preferably positioned at a well-defined focal point (position) within the cross-section of the channel and such focal point is selected appropriately with respect to the electrodes of the impedance detection system to maximize the signal from the cells and the contrast between the cells. Secondly, the cells are ideally aligned uniformly with respect to the electrodes. This reduces the spread of errors when measuring a single sub-population of cells and enables more robust separation of the mixed cells into the segregated sub-populations. Thirdly, it typically allows for the configuration of the excitation and detection electrodes that is most suitable for the identification of cells using impedance cytometry and cannot be achieved within the limitations of a conventional planar microfluidic chip. We describe how the chip can be manufactured. We further describe how this impedance cytometry microfluidic chip could be integrated with optical detection system so that each cell is analyzed by both, impedance and optical measurements thus reducing the CV from the population of cell and improving the cell separation.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

The present disclosure is based on extensive work conducted by the inventors on detection of impedance changes resulting from passing single cells in proximity to excitation and detection electrodes. As a cell passes in between the electrodes, its signal can be represented by the amplitude and phase of the AC current signal induced on the detection electrode (electrodes). Therefore, a single point on X-Y diagram as shown in FIG. 1 can represent the signal from a single passing cell. Along the X and Y axis on the diagram one could plot the amplitude and phase of the signal measured on the detection electrodes or alternatively some values representing mathematics functions of the amplitude and phase. If a population of cells passes along the channel, each cell contributes one point to the X-Y diagram as shown in FIG. 1a. If the cell position or cell orientation with respect to the electrodes changes, its effect on impedance signal on the detection electrode (electrodes) change as well.

Figure 1B:
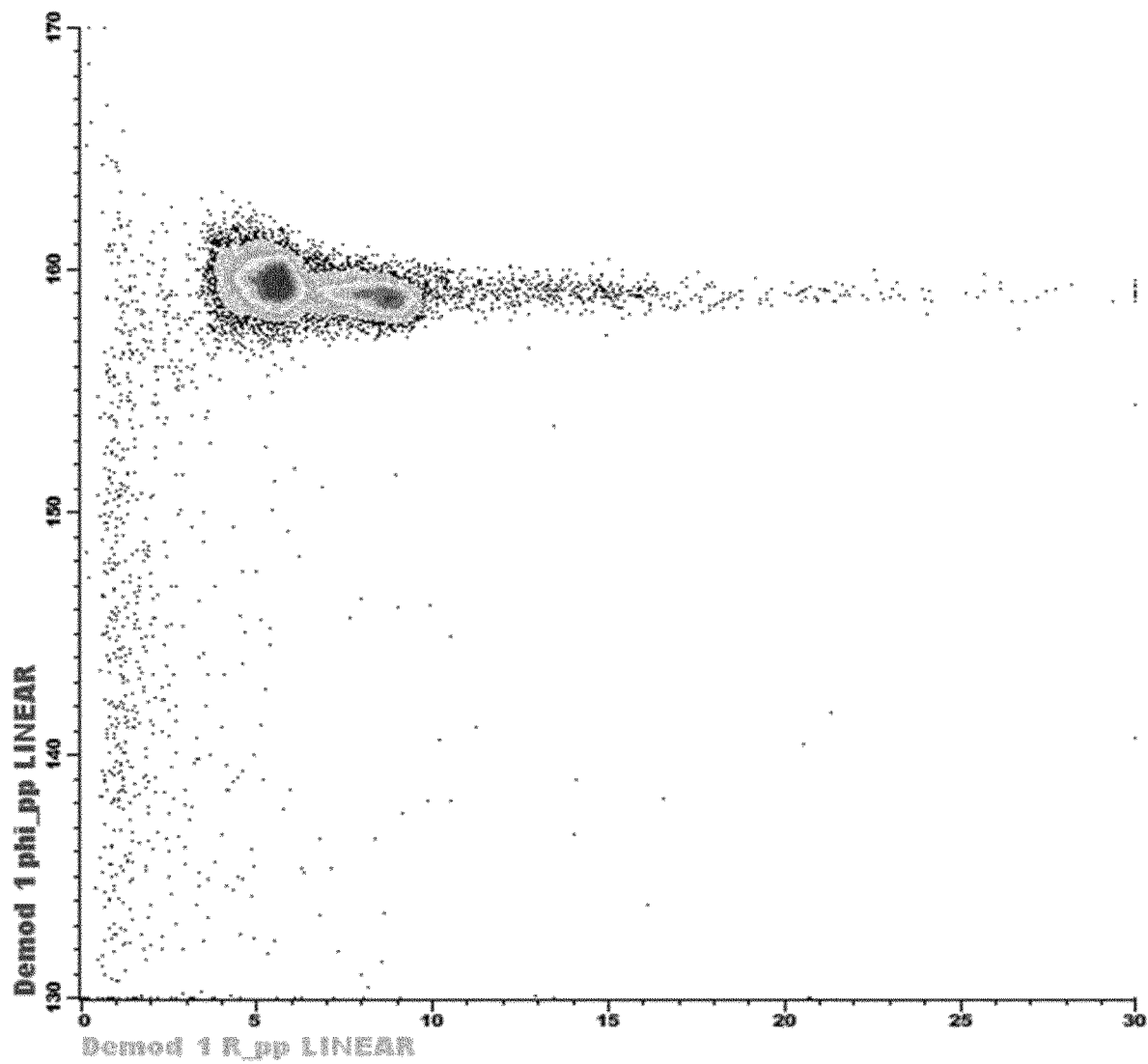
FIG. 1b. Scatter plot of data points resulting from measurements of a population of cells consisting of two sub-populations where such cells travel in a well-focused flow through the detection zone. The data points spread is much reduced and the separation of cells into two sub-populations is possible in this case.

To achieve selectivity of different cell types, one need to achieve accurate positioning of cells as they pass between the electrodes. Therefore, if one passes a population of cells in a microfluidic channel, the better the control in the position of each cell with respect to the electrodes, the smaller is the spread in the data points. This is due to intrinsic non-uniformity of an electrical field between electrodes of finite width and depth. FIG. 1a and FIG. 1b show the results of the impedance changes in the microfluidic chip with population of cells composed of two different types of cells (two sub-populations) flowing with poor positioning (FIG. 1a) and good positioning (FIG. 1b). The separation of cells into two sub-populations becomes possible if the position of the cells within the channel with respect to the electrodes is well defined. The same applies to the orientation of the cells within the channel. If the cells are substantially not spherical, but rather are anisotropic in shape, as is the case with semen cells and many other types of cells, it is desirable to align all the cells in the same position with respect to the electrodes. For example, if the cells are elongated, it could be desirable to align them all with the elongated direction facing the excitation electrode. This is because the difference in the alignment of the cells with respect to the electrodes has effect on the value of the impedance signal.

We will refer to better positioning of the cells within the channel and more homogeneous alignment of cells within the channel (if they are anisotropic) as better organizing the cells within the channel. Such organizing should be maintained in the detection zone, in the area close to the electrodes of the impedance detection system.

Figure 2:
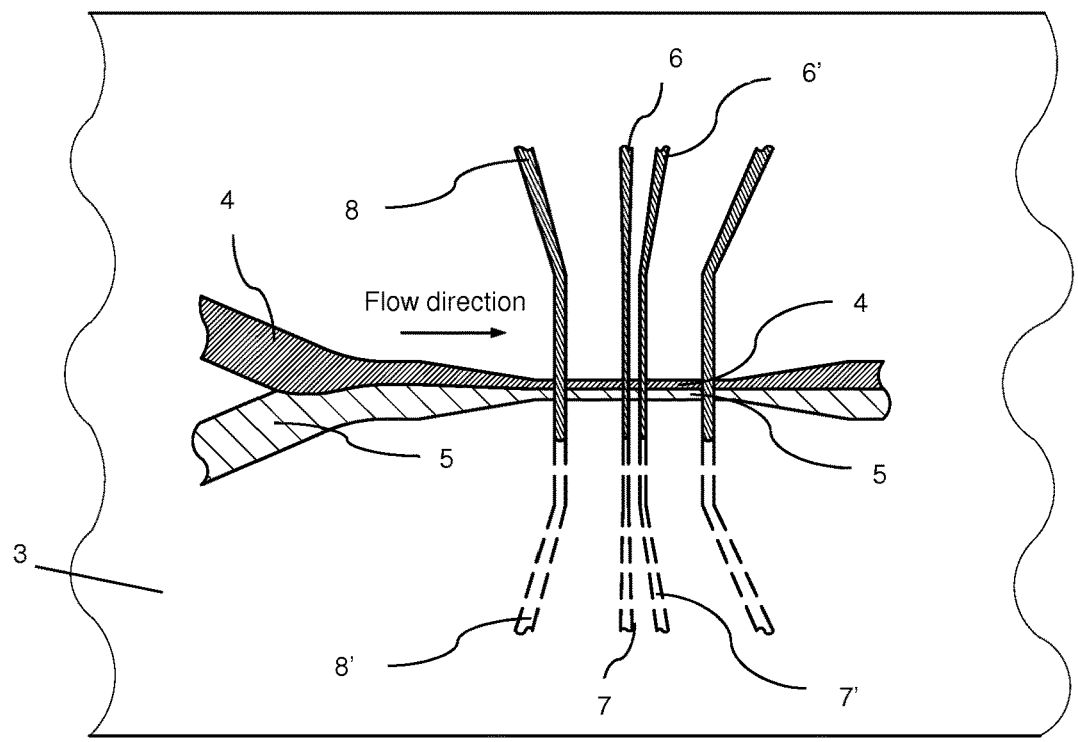
FIG. 2 Hydrodynamic focusing in a microfluidic channel with two flows merging: the sample fluid 4 flow and the sheath fluid flow 5.
Figure 3:
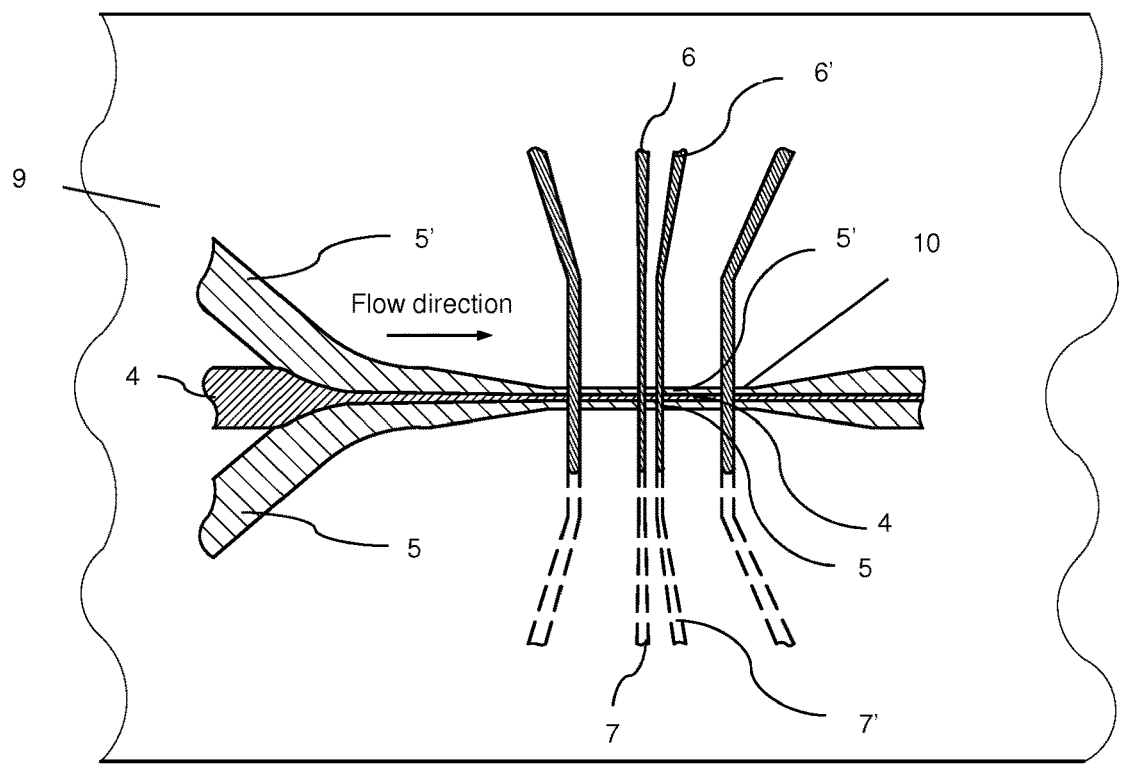
FIG. 3 Hydrodynamic focusing in a microfluidic channel with three flows merging: the sample fluid 4 flow is flanked on each side by a sheath fluid flow 5 and 5'.

To achieve the organizing of cells within the channel it is desirable to use hydrodynamic focusing. The easiest way to achieve hydrodynamic focusing in a microfluidic chip format is by merging the fluid containing the cells (sample fluid 4) with the sheath fluid 5. The sheath fluid can be injected from one side of the sample fluid (FIG. 2 indicated by numeral 5) or from both sides of the sample fluid (FIG. 3 indicated by numerals 5 and 5'). In both cases, the 2D hydrodynamic focusing is achieved. The problem with this approach is that as one pair of the electrodes 6 and 6' is located above the channel and the other one is below the channel 7 and 7' (shown in FIGS. 2 and 3), such hydrodynamic focusing does not achieve the positioning of the cells with respect to their distance from one of the electrodes. This increases the spread in values of the signal of the impedance change caused by passing of the cells and does not improve the spread in the data points.

Figure 4:
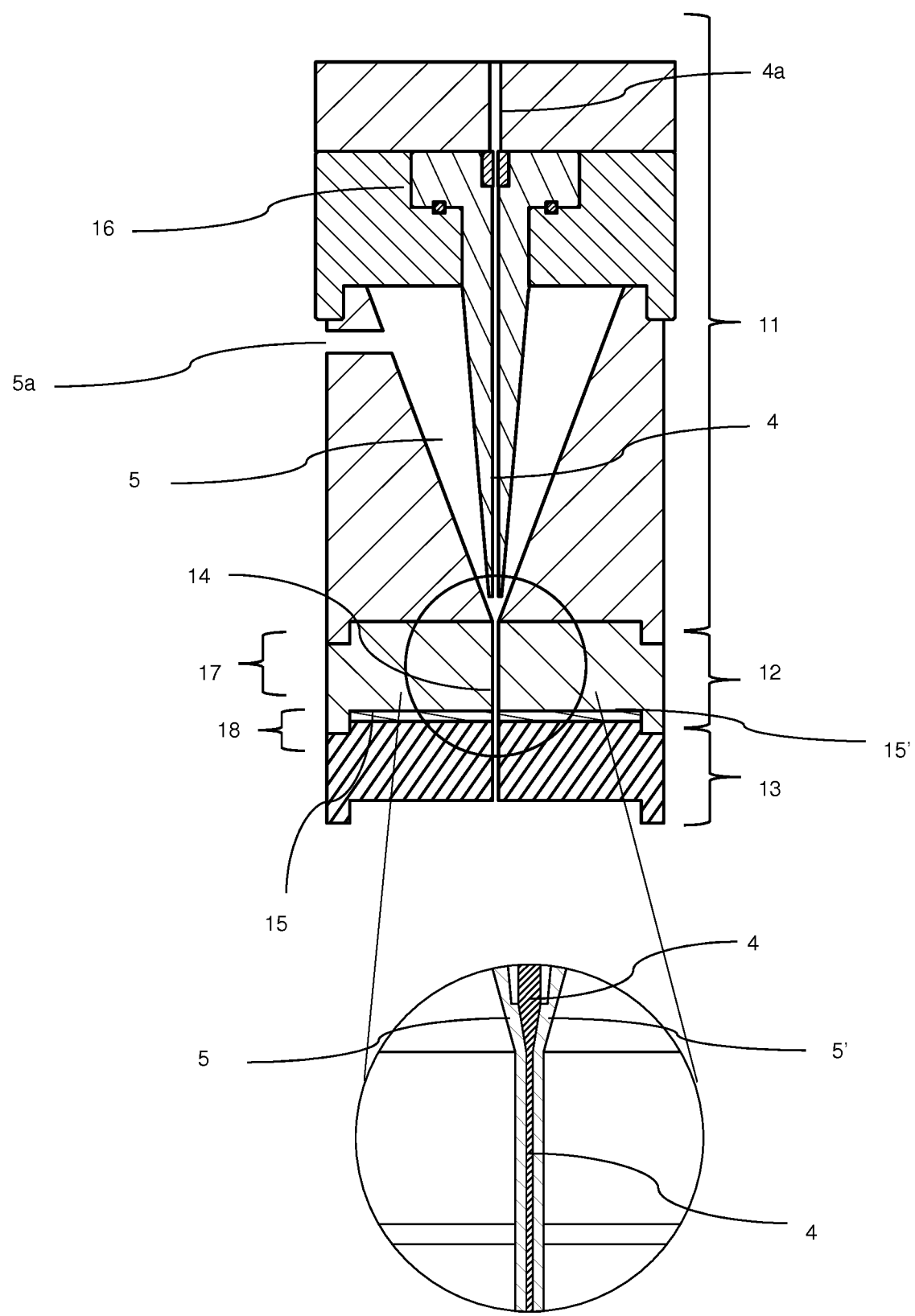
FIG. 4 Cross section along the axis of the channel
Figure 5:
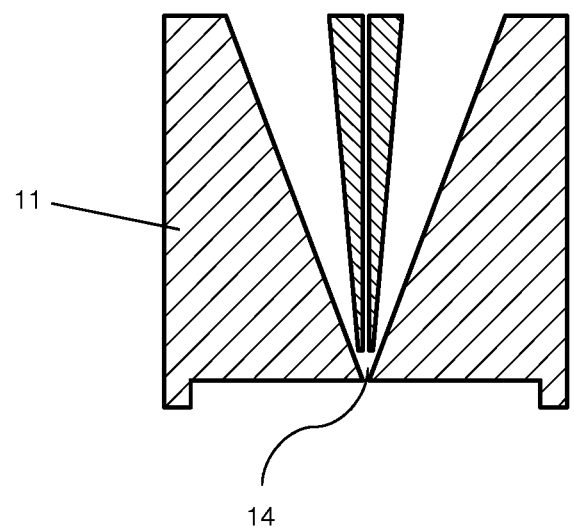
Figure 5:
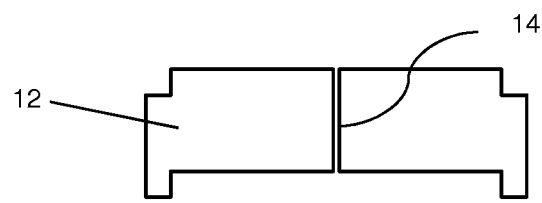
Figure 5:
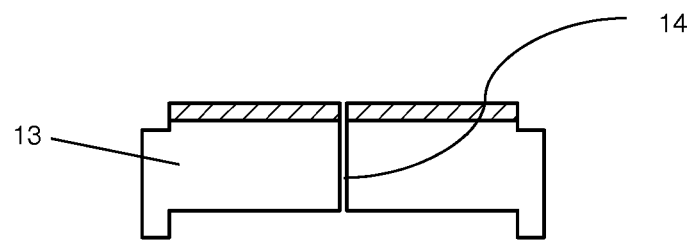

An embodiment presented in FIG. 4 is an apparatus comprising a channel 14, a hydrodynamic focusing nozzle 11 and electrodes of the impedance measurements system 15 and 15'. In this embodiment, all the electrodes of the impedance measurement system are located in one geometrical plane. The electrodes could have the thickness in the range of 5 micrometers to 300 micrometers. Greater thickness of the electrodes creates more homogeneous electric field in the detection zone, but does not allow detecting smaller cells as it increases chances of two cells passing the detection electrode at the same time. Typically, the thickness of electrodes is chosen in respect to the cell size that needs to be detected, smaller cells require smaller electrodes and larger cells correspondingly larger electrodes. The electrodes 15 and 15' go through the walls of the channel 14 to make electrical contact with the fluid within the channel. The cell detection zone 18 is the zone proximal to the location where the electrodes go through the wall of the channel. The detection zone 18 is separated from the proximal end of the hydrodynamic focusing nozzle 11 by an optional spacer zone 17 that could be in the range of 0.1-2 mm along the channel. Larger spacer zone will lead to potential defocusing of sample stream and therefore would lead to impedance signal variation. The cross-section of the channel 14 in the spacer zone 17 and the detection zone 18 might not be identical. FIG. 4 shows the case when they are essentially identical. The benefit of this configuration of the microfluidic chip is that it can be readily manufactured. For this the elements of the microchip could be manufactured separately by thick photoresist lithography (SU-8 photoresist lithography), consisting of section 11, section 12 and section 13. Each of these sections contains the channel as shown in FIG. 5a, b, c, indicated by numeral 11, 12, and 13. Section 13 contains electrodes, in this embodiment two electrodes are shown. In this way, it is easy to mount the electrodes on the flat facet of the section 13. The electrodes protrude into the channel by a distance that is small compared with the diameter of the channel. In this embodiment, the channel is of circular shape. Section 11 contains the nozzle of the hydrodynamic focusing system. The three sections are positioned so that the sections of channels 14 in each of them are co-axial and finally bonded together to form one continuous hermetically sealed channel. FIGS. 4 and 5 do not show further sections of the chip where the cells are separated into A and B subpopulations. The sections 11, 12 and 13 are made of a polymer material for example such as PMMA or polycarbonate.

The cross-sectional area of the channel 14 is in the range of 0.0001-0.25 mm$^2$. The flow rate of the sample fluid 4 through the channel is in the range of 0.1-100 ul/min and flow rate of the sheath fluid 5 is in the range of 1-1000 ul/min.

Figure 6:
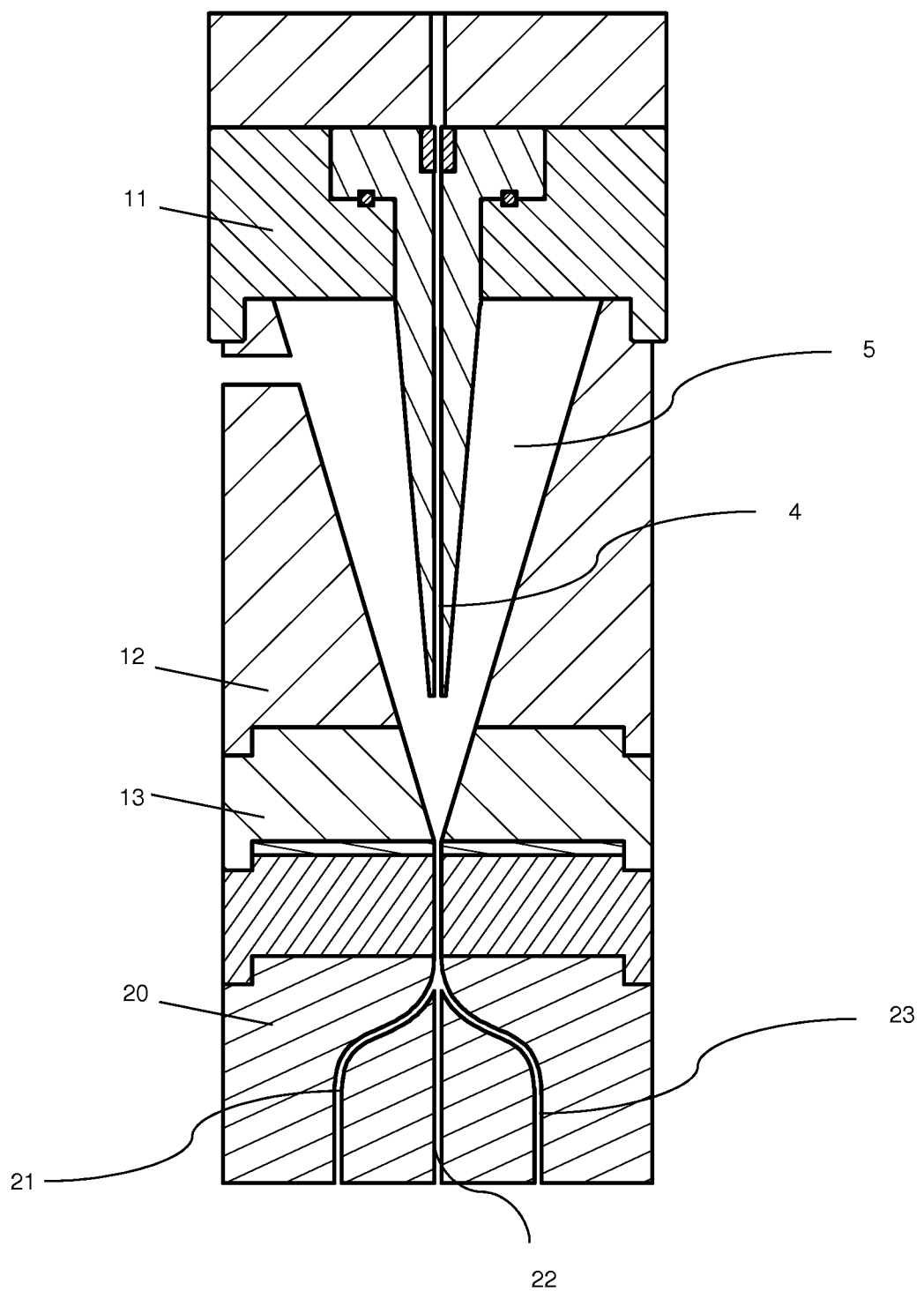
FIG. 6. Embodiment of the apparatus with varying cross-section of the channel along its length.

The cross section of the channel 14 in the spacer zone 17 can be identical to the channel 14 in the detection zone 18. Alternatively, they can be different. FIG. 6 shows the embodiment where channel is the spacer zone 12 has greater cross-section than in the detection zone 13. The channel 14 in each zone does not have to have a constant cross-section throughout the thickness of the zone. For example, FIG. 6 shows embodiment where the channel in the spacer zone has decreasing cross section throughout the thickness of the spacer zone 12 forming a funnel shape channel. Further, FIG. 6 shows separation zone 20 where the channel is split into three channels: channel 21 for collecting the population A, Channel 22 for collecting the population B and channel waste 23 for collecting the unidentified semen. The electrodes in the detection zone 13 and the separation means in the separation zone are not shown. The channel also does not need to be of circular cross-section. It could be e.g. of oval cross-section or indeed other cross-section. Again, the cross-section of the channel in the separation zone does not need to be identical to the one in the detection zone or in the spacer zone. The length of the spacer zone could be in the range of 0.05-2 mm, the length of the detection zone could be in the range of 0.05-2 mm and the length of the separation zone could be 0.05-2 mm.

FIG. 7 shows one element of another embodiment of the apparatus. In this embodiment, there is an array of eight electrodes positioned in the detection zone 13, all located in the same plane. In this embodiment, the two electrodes out of eight are excitation electrodes 7 and 7'. They are energized by AC signals at frequencies f1 and f2 respectively and are shown as shadowed. There other six electrodes are the detection electrodes 6, all connected to separate channels of lock-in amplifiers. Each of them detects the signals at frequencies f1 and f2, making it the total of 12 signals, each composed of the amplitude and phase characteristics. The positions of the cells and identification of the cells is achieved from the 24 signals received. FIG. 7 does not show the connection of the electrodes to the AC voltage sources and lock-in amplifiers.

Another number of electrodes could be used and these could be subdivided into excitation and detection electrodes in different ways. For example, one could construct embodiment with one excitation electrode and seven detection electrodes or a combination of four-plus-four: four excitation electrodes and four detection electrodes.

Figure 8:
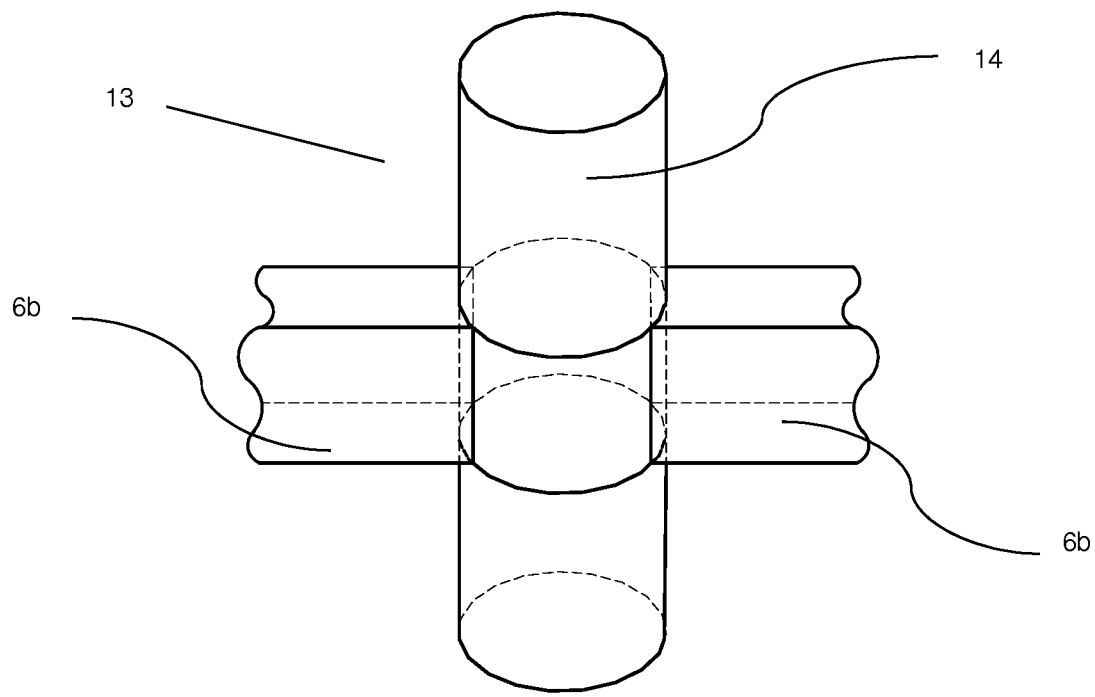
FIG. 8. Channel with two electrodes in the detection zone.

In another embodiment, the electrodes 6b and 6b' could enter into the channel and be positioned along the inner wall of the channel 14 (FIG. 8). This will increase the region of the homogeneous electric field within the channel and therefore will increase the size of the detection area and the homogeneity of signal detected from a cell, thus decreasing the spread in data points from a population of identical cells. FIG. 8 shows detection zone of the embodiment with two such electrodes. The electrodes positioned on the inner walls of the channel could have the size of 0.0001-0.01 mm$^2$. Similarly, embodiment with other numbers of electrodes could be constructed. FIG. 8 does not show the connection of the electrodes to the AC voltage source and the lock-in amplifier.

Figure 9:
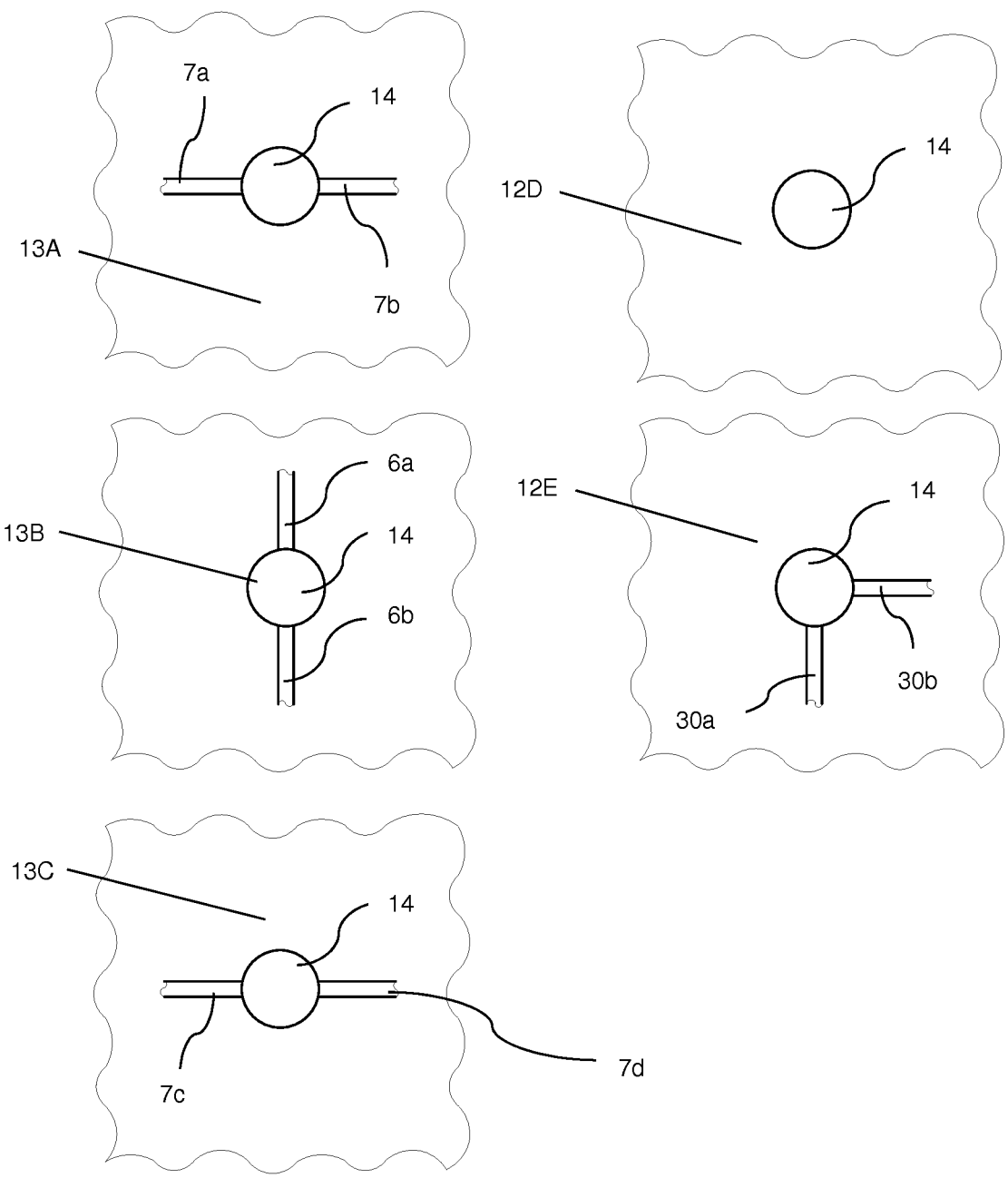
FIG. 9. Embodiment of the apparatus containing six electrodes positioned in three planes and also two spacer layers, D and E positioned in between the planes with electrodes. One of the spacer layers, the layer E, contains two optical waveguides directed at the angle of some 90 degrees to each other, both facing into the channel.

In another embodiment the electrodes could be placed not all in the same plane. FIG. 9 shows embodiment where electrodes are located in three different planes, called, planes, 13A, 13B and 13C. Spacer layers 12D, and 12E separate these planes. The spacer 12D is positioned in between the planes 13A and 13B. The spacer 12E is positioned in between the planes 13B and 13C. The channel 14 penetrates through all these planes. The separation of the electrodes into the excitation electrodes and the detection electrodes could be different in different embodiments. For example, two electrodes in Plane 13B could be excitation electrodes 6a and 6b and four electrodes in planes 13A and 13C could be the detection electrodes 7a, 7,b, 7c and 7d. The thickness of the spacer layers 12D and 12E could be in the range of 0.05-2 mm. The apparatus could be equipped by optical waveguides 30a and 30b. The light is coupled into the waveguide. The train of particles passes through the light source. The second waveguide collects the light either scattered by the cells or alternatively, a fluorescence signal could be collected. The two waveguides could face each other or alternatively, they could be at an angle to each other. The position of the waveguides with respect to each other is defined by the type of optical measurements to be performed: e.g. fluorescence detection, small angle scatter, large angle scatter. The two waveguides could be positioned in the same plane or alternatively, they could be positioned in different planes in the detection zone. FIG. 9 shows embodiment where the two optical waveguides 30a and 30b are positioned in the same plane and are directed at the angle of 90 degrees with respect to each other. Other numbers of waveguides could be used.

It may be advantageous to device hydrodynamic focusing nozzle so that it achieves preferential alignment of the cells within the channel with respect to the electrodes. Many cells are anisotropic, i.e. they are not spherically symmetric. The semen cells are a good example of this. If the cells have preferential ellipsoid shape or preferential discoid shape, the response in the detection zone from each of the cell depends on its orientation with respect to the excitation and detection electrodes. For example, the response will be different depending on whether the long axis of the ellipsoid is aligned along the line joining the excitation and detection electrodes, or perpendicular to such a line. Therefore, it is important to achieve the uniformity of the alignment of all cells with respect to the electrodes.

Figure 10:
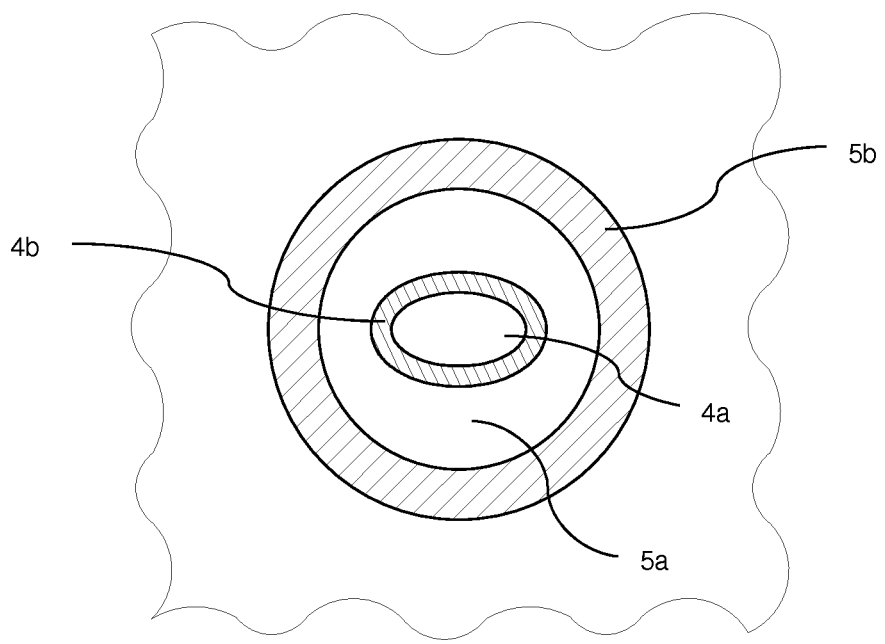
FIG. 10. Cross-section of the hydrodynamic focusing system with the inner nozzle of the sample fluid channel having elliptical shape and the outer nozzle of the sheath fluid channel having circular shape.

This alignment of cells could be achieved using the hydrodynamic focusing nozzle. FIG. 10 shows one such embodiment viewed along the axis of the nozzle from the tapered side. The nozzle is composed of two channels. The inner channel, the sample fluid channel 4a is of smaller cross-section than the outer channel 5a, the sheath fluid channel. The inner channel 4a could be of asymmetric shape, e.g. elliptical shape. The inner and outer channels could be tapered. The output orifice of the sample fluid channel 4a is hydraulically coupled to the channel of the spacer zone 12. If the spacer zone 12 is absent in the embodiment, then the output orifice is coupled to the channel 14 of the detection zone 13. The elliptical shape of the orifice enables alignment of the cells in the channel 14. Elongated axis of the output orifice is positioned in a particular way with respect to positions of electrodes 15 in the channel. In this embodiment, the output orifice of the sheath fluid channel 5a could be circular.

Figure 11:
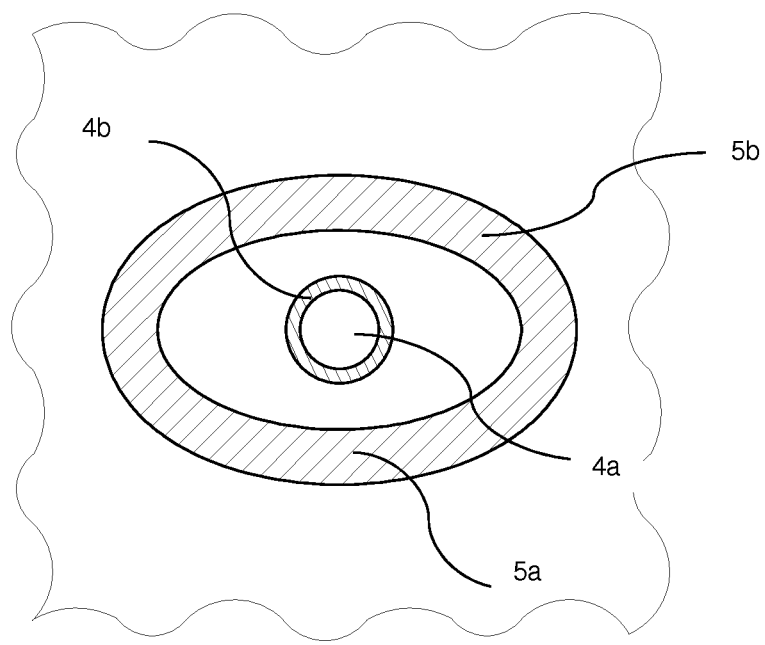
FIG. 11. Cross-section of the hydrodynamic focusing system with the inner nozzle of the sample fluid channel having circular shape and the outer nozzle of the sheath fluid channel having elliptical shape.

In another embodiment, the output orifice 4b of the sample fluid channel 4a could be circular and the output orifice 5b of the sheath fluid channel 5a could be asymmetric, e.g. elliptical. In this case, the alignment of the cells within the channel is achieved by the flow of the sheath fluid 5. This embodiment is shown in FIG. 11. The advantage of this approach is that realignment of the cells is achieved by the anisotropic action of the sheath fluid flow as opposed to a more damaging action of letting the cells though an elliptical constriction of the sample fluid channel 4 as in FIG. 10.

Figure 12:
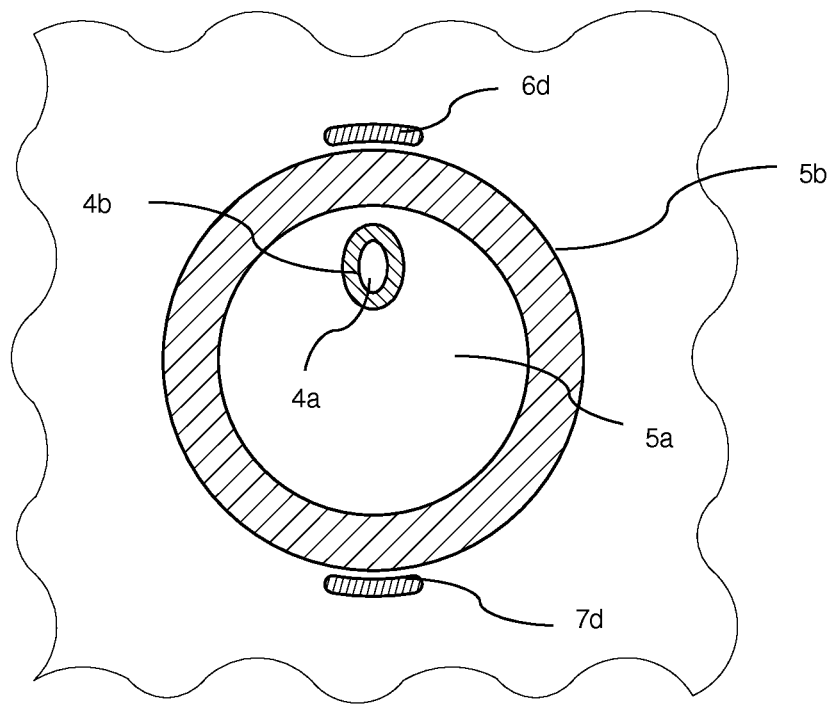
FIG. 12. Cross-section of the hydraulic focusing system with the inner nozzle of the sample fluid channel displaced with respect to the center of the sheath fluid elliptical channel towards the excitation electrode.

In embodiment shown in FIG. 12 the elliptical inner nozzle 4b of the hydrodynamic focusing system is displaced with respect to the center of the circular shape nozzle 5b of the sheath fluid channel. The sample fluid flow 4 is displaced from the center of the channel towards the excitation electrode 6d. The cross-section of the nozzle is shown along with the positions of the excitation 6d and detection 7d electrodes.

Figure 13:
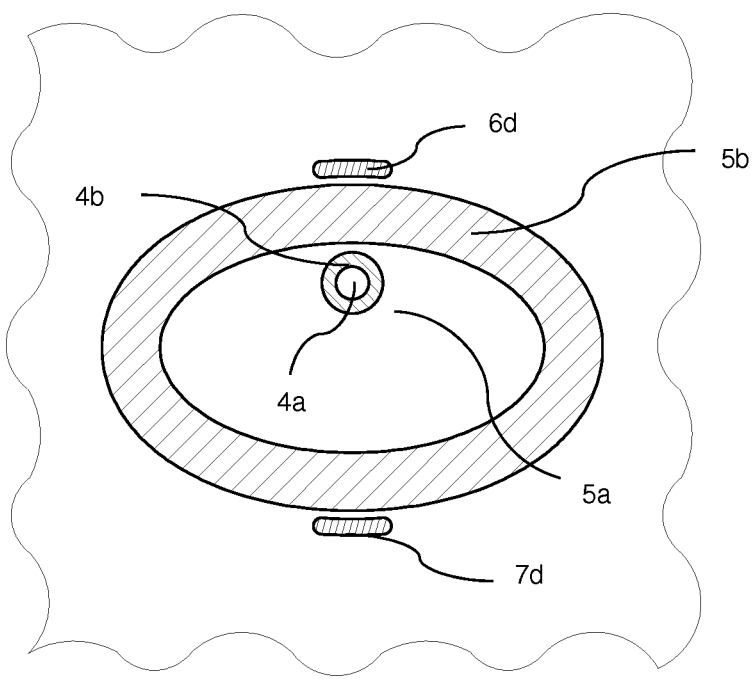
FIG. 13 Cross-section of the hydraulic focusing system with the elliptical shape inner nozzle of the sample fluid channel displaced with respect to the center of the circular sheath fluid channel towards the excitation electrode.

In embodiment shown in FIG. 13 the inner nozzle 4b of the hydrodynamic focusing system is displaced with respect to the center of the elliptical shape nozzle 5b of the sheath fluid channel. The sample fluid flow 4 is displaced from the center of the channel towards the excitation electrode 6d. The cross-section of the nozzle is shown along with the positions of the excitation 6d and detection 7d electrodes.

Figure 14:
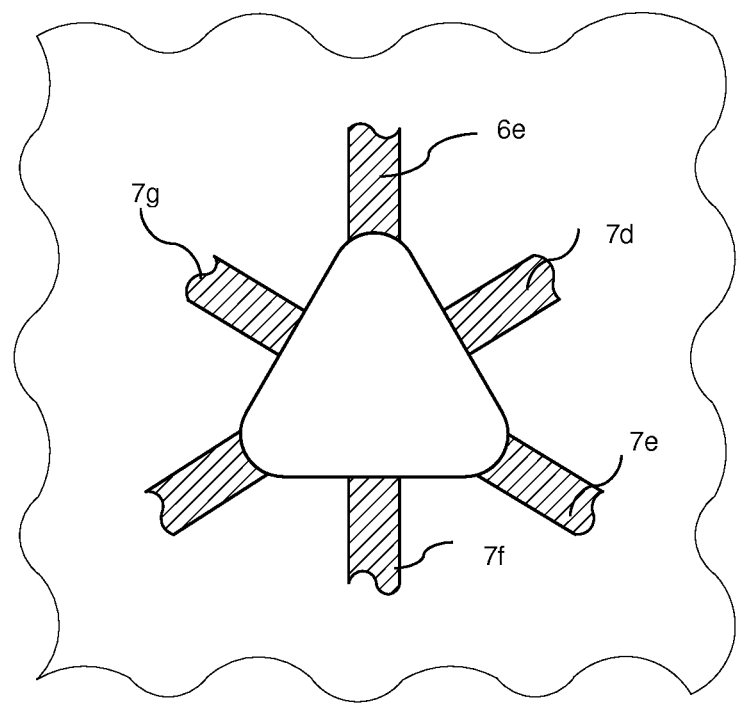
FIG. 14 Cross-section of the channel of an approximately triangular geometry with one excitation electrode and several detection electrodes.
Figure 15:
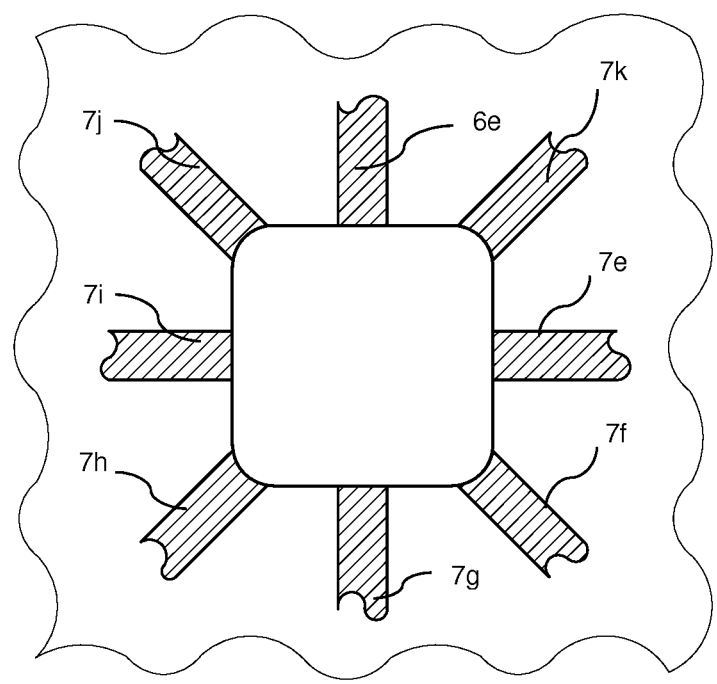
FIG. 15 Cross-section of the channel of an approximately square geometry with one excitation electrode and several detection electrodes.

FIGS. 14 and 15 show embodiments with the channel of a non-circular cross-section. Positions of the electrodes are indicated on the drawings.

To illustrate the method of impedance measurement with hydrodynamic focusing according to presented invention we have carried out experiments with mixed population of leukocytes. This example of detection of impedance changes resulting from passing single cells in proximity to excitation and detection electrodes is displayed in FIGS. 16a and 16b.

Figure 16A:
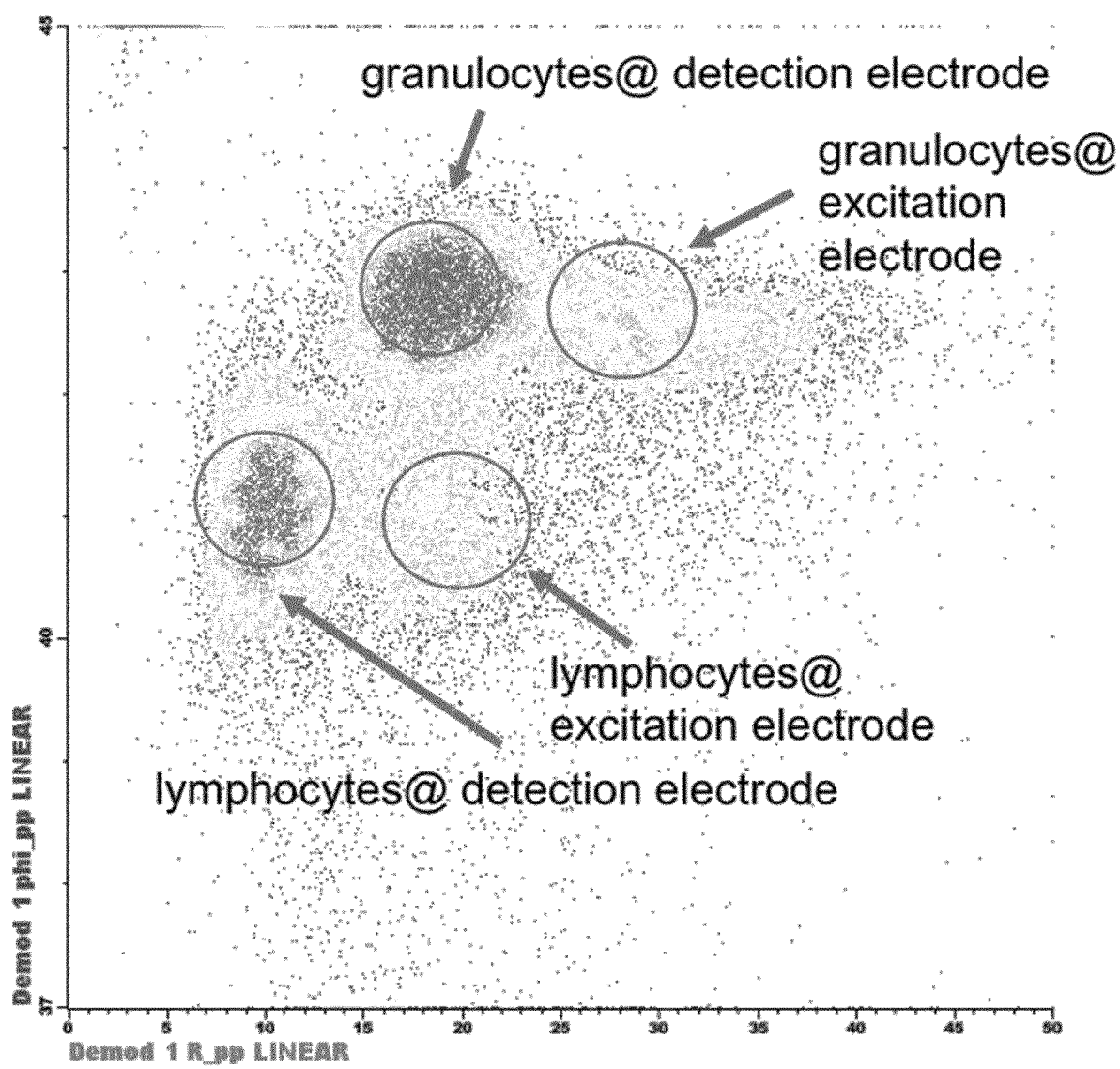
FIG. 16a Scatter plot of data points resulting from measurements of a population of leukocyte cells consisting of sub-populations where such cells travel in a poorly focused flow though the detection zone.
Figure 16B:
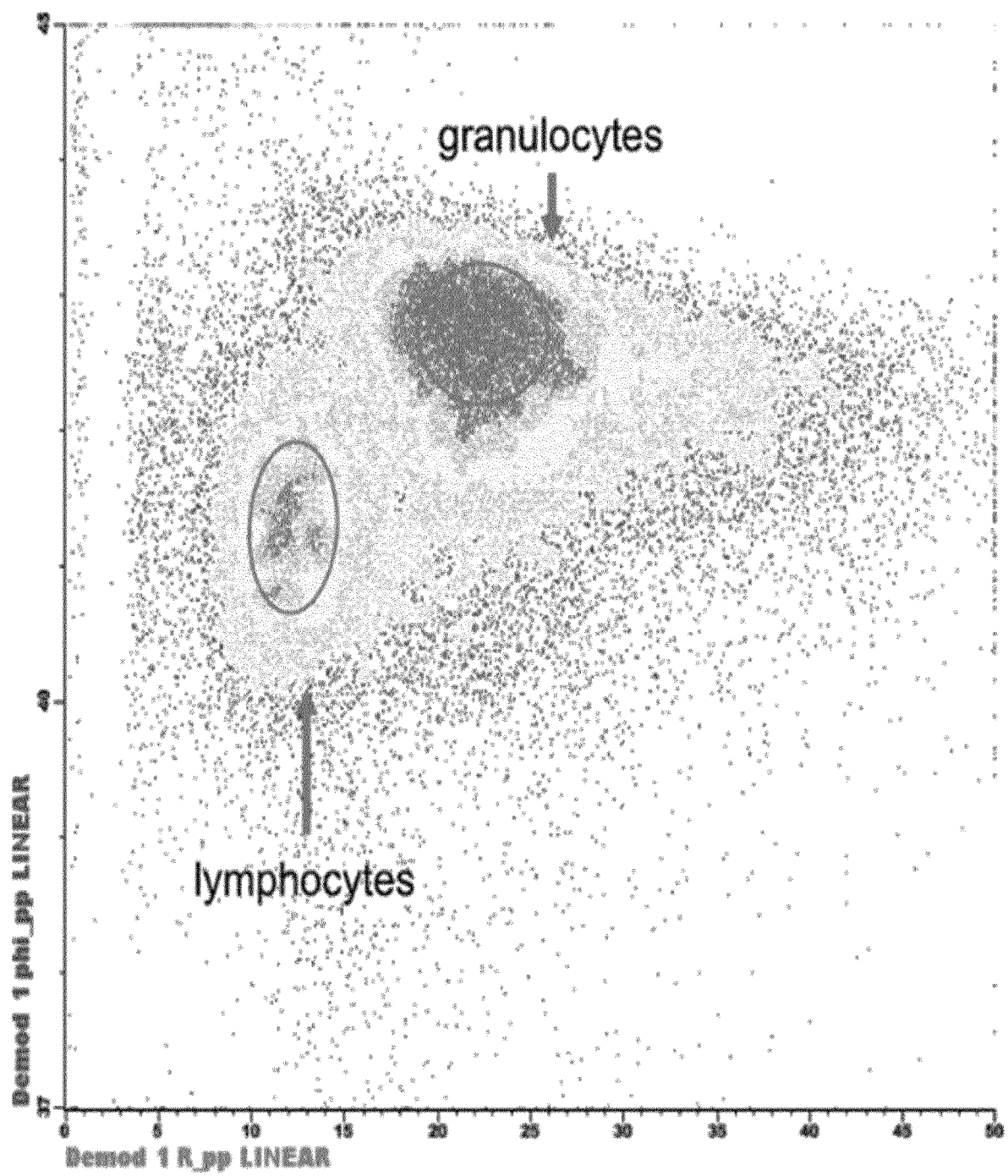
FIG. 16b. Scatter plot of data points resulting from measurements of a population of leukocyte cells consisting of sub-populations where such cells travel in a well-focused flow though the detection zone. The data points spread is much reduced in this case.

Similarly to the FIGS. 1a and 1b as a cell passes in between the electrodes, its signal can be represented by the amplitude and phase of the AC current signal induced on the detection electrode (electrodes). Therefore, a single point on X-Y diagram as shown in FIG. 16 can represent the signal from a single passing cell. Along the X and Y axis on the diagram one could plot the amplitude and phase of the signal measured on the detection electrodes or alternatively some values representing mathematics functions of the amplitude and phase. If a population of cells passes along the channel, each cell contributes one point to the X-Y diagram as shown in FIG. 16a and FIG. 16b. In this particular example, we have passed mixed population of leukocytes (white blood cells). This mixed population in particular consists of three subpopulations: granulocytes, lymphocytes and monocytes which are often referred in haematology as 3-part differential populations of white blood cells. Correct counting of cell number in each subpopulation, counting of the proportion of each population and average volume of leukocytes are very important in haematology analysis. As previously described, if the cell position or cell orientation with respect to the electrodes changes, its effect on impedance signal on the detection electrode (electrodes) change as well. FIG. 16a and FIG. 16b show the results of the impedance changes in the microfluidic chip with populations of white blood cells flowing with poor positioning and not hydrodynamic focusing (FIG. 16a) and good positioning with hydrodynamic focusing (FIG. 16b). As displayed in FIG. 16a it is possible to separate between the granulocyte and lymphocyte populations, but each of the cell populations are presented as double populations corresponding to proximity to excitation and detection electrodes respectively. This reduce accuracy of leukocyte volume measurement, coefficients of variation (CV %) are 26.55 for granulocyte population volume measurement and 32.62% for lymphocyte volume measurement. These measurements inherently vary, as the cells in populations are not homogeneous, but moreover an additional variation is introduce by the differences in impedance measurements in respect to proximity to excitation and detection electrodes. In case of FIG. 16b we have used hydrodynamic focusing the position of the cells within the channel with respect to the electrodes is well defined. We do not observe double populations of granulocytes and lymphocytes. Additionally, the variation of cell volume measurement is reduced to 18% for granulocytes and 17.2 percent for lymphocytes.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

REFERENCES

1. U.S. Pat. No. 5,135,759, "Method to preselect the sex of offspring", Johnson et. al., Apr. 26, 1991
2. U.S. Pat. No. 6,782,768 B2, "Flow cytometry nozzle", Buchanan et. al., Aug. 12, 2003
3. H. M. Shapiro, "Practical Flow Cytometry", John Wiley and Sons, Hoboken, New Jersey, 2003

4. W. H. Coulter, "High Speed Automatic Blood Cell Counter and Cell Size Analyser", Proc. Natl. Electron. Conf. 1956, 12 1034-1040
5. S. Gawad, L. Schild, P. H. Renaud, "Micromachined impedance spectroscopy flow cytometer for cell analysis and particle sizing", Lab. Chip. 2001 1 76-82
6. T. Sun and H. Morgan, "Single-cell microfluidic impedance cytometry: a review", Microfluidics and Nanofluidics, 2010, 8, 423-443
7. JP200310799, "Microchip and device for classifying particles", Takanori et. al., Apr. 9, 2003
8. R. Rodriguez-Trujillo, C. Mills, J. Samitier, G. Gomila, Microfluidics and Nanofluidics, 3 171, 2007
9. P. Walsh, E. Walsh, M. Davies, Int. J. Heat Fluid Flow 28 44, 2007
10. R. Scott, P. Sethu, C. K. Harnett, "Three-dimensional hydrodynamic focusing in a microfluidic Coulter counter", Rev. Sci. Instruments 79 046104, 2008
11. Y. J. Chiu, S. H. Cho, Z. Mei, V. Lien, T. F. Wu, Y. H. Lo, "Universally applicable three-dimensional hydrodynamic microfluidic flow focussing", Lab on a Chip 2013 13 1803
12. US 2009/0283148 A1, "Microchip and channel structure for the same", Shinoda et. al., May 4, 2009
13. US2014/273192A1, "System for high throughput sperm sorting", Sharpe et. al., Mar. 14, 2013
14. "An Introduction to Fluid Dynamics", Batchelor G. K., Cambridge University Press, pp. 211-215, 1967
15. "Microfluidic Cell Sorting: A Review of the Advances in the Separation of Cells from Debulking to Rare Cell Isolation", C. Wyatt Shields I V et al, Lab Chip. 2015 Feb. 16, 15(5): 1230-1249
16. US2005/0118705, "Electrical detectors for microanalysis", Rabbit et al.
17. EP2995961, "Flow channel device, analytical apparatus, and fluid apparatus", Yoichi et al.

The invention claimed is:

1. A microfluidic chip for microfluidic flow analysis of a particulate containing fluid, the microfluidic chip comprising:
    at least two layers;
    a microfluidic channel that is substantially orthogonal to a plane of the layers of the chip comprising a fluid inlet for receipt of a stream of particulate containing fluid; and
    a detection zone comprising at least one pair of electrodes in electrical communication with the microfluidic channel,
    wherein the at least one pair of electrodes comprise an excitation electrode coupled to an AC signal source and a detection electrode configured to detect AC impedance changes in the microfluidic channel between the electrodes resulting from particles passing between the electrodes in the microfluidic channel,
    wherein the microfluidic channel is a straight channel that extends through the at least two layers of the microfluidic chip, and
    wherein the detection zone spans at least one of the layers of the microfluidic chip.

2. A microfluidic chip as claimed in claim 1 in which the detection zone comprises a plurality of pairs of electrodes in the same detection plane.

3. A microfluidic chip as claimed in claim 1 in which the pairs of electrodes are arranged radially around the microfluidic channel.

4. A microfluidic chip as claimed in claim 1 in which an excitation electrode of an electrode pair is disposed in one layer of the chip and a detection electrode of the same electrode pair is disposed in a second layer of the chip.

5. A microfluidic chip as claimed in claim 1 where the detection zone of the microfluidic chip contains at least two optical waveguides, at least one of these is coupled to a light source and the other one is coupled to an optical detector to detect optical signal resulting from the particulates and such optical signal is measured in conjunction with the electrical signal detected at the detection electrode to improve the CV of the data points from a population of particulates.

6. A microfluidic chip as claimed in claim 1 in which the AC signal is composed of at least two different frequencies and is applied to the excitation electrodes, and the detection electrodes detect impedance change caused by single passing particulates at these very same frequencies and a particulate is attributed to X or Y sub-population on the basis of amplitude and phase signals detected at the detection electrodes at each of these frequencies.

7. A microfluidic chip for microfluidic flow analysis of a particulate containing fluid, the microfluidic chip comprising:
    at least two layers;
    a microfluidic channel that is substantially orthogonal to a plane of the layers of the chip comprising a fluid inlet for receipt of a stream of particulate containing fluid; and
    a detection zone comprising at least one pair of electrodes in electrical communication with the microfluidic channel,
    wherein the at least one pair of electrodes comprise an excitation electrode coupled to an AC signal source and a detection electrode configured to detect AC impedance changes in the microfluidic channel between the electrodes resulting from particles passing between the electrodes in the microfluidic channel, wherein
    the pairs of electrodes are arranged radially around the microfluidic channel.

8. The microfluidic chip of claim 7 in which an excitation electrode of at least one of the electrode pairs is disposed in one layer of the chip and a detection electrode of the same electrode pair is disposed in a second layer of the chip.

9. The microfluidic chip of claim 7, in which the detection zone comprises a plurality of pairs of electrodes in a same detection plane.

10. The microfluidic chip of claim 7, where the detection zone of the microfluidic chip contains at least two optical waveguides, at least one of these is coupled to a light source and the other one is coupled to an optical detector to detect optical signal resulting from the particulates and such optical signal is measured in conjunction with the electrical signal detected at the detection electrode to improve the CV of the data points from a population of particulates.

11. The microfluidic chip of claim 7, in which the AC signal is composed of at least two different frequencies and is applied to the excitation electrodes, and the detection electrodes detect impedance changes caused by single passing particulates at these very same frequencies and a particulate is attributed to X or Y sub-population on the basis of amplitude and phase signals detected at the detection electrodes at each of these frequencies.

12. A microfluidic chip for microfluidic flow analysis of a particulate containing fluid, the microfluidic chip comprising:
    at least two layers;

a microfluidic channel that is substantially orthogonal to a plane of the layers of the chip comprising a fluid inlet for receipt of a stream of particulate containing fluid; and a detection zone comprising at least one pair of electrodes in electrical communication with the microfluidic channel, wherein the at least one pair of electrodes comprise an excitation electrode coupled to an AC signal source and a detection electrode configured to detect AC impedance changes in the microfluidic channel between the electrodes resulting from particles passing between the electrodes in the microfluidic channel, and the detection zone of the microfluidic chip contains at least two optical waveguides, at least one of these is coupled to a light source and the other one is coupled to an optical detector to detect optical signal resulting from the particulates and such optical signal is measured in conjunction with the electrical signal detected at the detection electrode to improve the CV of the data points from a population of particulates.

13. The microfluidic chip of claim 12, in which the detection zone comprises a plurality of pairs of electrodes in a same detection plane.

14. The microfluidic chip of claim 12 in which an excitation electrode of at least one of the electrode pairs is disposed in one layer of the chip and a detection electrode of the same electrode pair is disposed in a second layer of the chip.

15. The microfluidic chip of claim 12, in which the AC signal is composed of at least two different frequencies and is applied to the excitation electrodes, and the detection electrodes detect impedance changes caused by single passing particulates at these very same frequencies and a particulate is attributed to X or Y sub-population on the basis of amplitude and phase signals detected at the detection electrodes at each of these frequencies.

* * * * *